United States Patent [19]

Van Snick et al.

[11] Patent Number: 5,157,112
[45] Date of Patent: Oct. 20, 1992

[54] ANTIBODIES IMMUNOREACTIVE WITH THE T-CELL GROWTH FACTOR, P40

[75] Inventors: Jacques Van Snick, Brussels; Catherine Uyttenhove, Chaumont-Gistoux, both of Belgium; Richard J. Simpson, Melbourne, Australia

[73] Assignee: Ludwig Institute for Cancer Research, Switzerland

[21] Appl. No.: 408,155

[22] Filed: Sep. 15, 1989

Related U.S. Application Data

[63] Continuation-in-part of Ser. No. 246,482, Sep. 19, 1988.

[51] Int. Cl.⁵ ............................................. C07K 15/28
[52] U.S. Cl. .................................. 530/387.9; 530/351; 530/808; 530/388.23; 530/389.2; 930/141; 435/70.21; 435/172.2; 424/85.8; 935/89
[58] Field of Search ....................... 530/387, 808, 351; 435/70.21, 172.2; 424/85.8; 935/89; 930/141

[56] References Cited

U.S. PATENT DOCUMENTS

4,636,463  1/1987  Altman et al. ........................ 530/351
4,935,343  6/1990  Allison et al. ..................... 435/172.2

OTHER PUBLICATIONS

Van Snick et al., *Eur. J. Immunol* 15, 1985, pp. 1148–1151.
Rolenk et al., *J. Exp. Med*, 169, 1989, pp. 1693–1701.
Ohara et al., *Nature* 315, 1985, pp. 333–336.

*Primary Examiner*—Garnette D. Draper
*Attorney, Agent, or Firm*—Felfe & Lynch

[57] ABSTRACT

The present invention relates generally to a T cell growth factor. More particularly, the present invention relates to a T cell growth factor which comprises a glycoprotein which supports interleukin 2- and interleukin 4-independent growth of helper T cells especially from murine and human sources and further which is capable of augmenting proliferation of IL3- or IL4-responsive cells. Even more particularly, the present inventin relates to the helper T cell growth factor P40, pharmaceutical compositions thereof, antibodies thereto and recombinant DNA clones thereof. The present invention also contemplates a method for inducing the proliferation of helper T cells as well as IL3- and Il4-responsive cells. The helper T cells growth factor contemplated herein is useful in the stimulation of specific cells in the immune system, either alone or in combination with IL3 or IL4.

6 Claims, 14 Drawing Sheets

FIG. 4B

| | 1 | 2 | 3 | 4 | kDa |
|---|---|---|---|---|---|
| | | | | | — 94 |
| | | | | | — 67 |
| | | | | ● | — 43 |
| | | | | | — 30 |
| | | | | | — 20 |
| | | | | | — 14 |

```
         10         20         30        40
          '          '          '         '
                                *
QRCSTTWGIRDTNYLIENLKDDPPSKCSCSGXVTSCLCLSVPTDD

D2            D3
        dtnylienlkddppskcscsgxvtsclclsvptdd
                    D3-S1
                    ddppskcscsgxv
    T1/T2
    csttwgirdtnylienlkddppsk 50         60        70         80         90
     '          '         '          '          '
                *                               *
CTTPCYREGLLQLTXATQKSRLLPVFHRVKRIVEVLKXITCPSFS cttpcyregl
          D3-S2                          D3-S3
          gllqltxatqksrllpvfhrvkrivevlkxitcpsfs
          T3               T4         T5
          egllqltxatqk    llpvfhr    ivevlkxitcpsfs
                             C1
                             hrvkrivevlk 100        110       120
    '          '         '
    *
CEKPCXQTMAGNTLSFLKSLLGTFQKTEMQRQKSRP cekpcxqtma
              T6
cekpcxgtmagntlsflksllgtfqktemqr
              C2
              sflksllgtf
        CN1                        CN2
        gntlsflksllg               qrqksrp
```

FIG. 7

ANTIBODIES IMMUNOREACTIVE WITH THE T-CELL GROWTH FACTOR, P40

This application is a continuation-in-part of Ser. No. 246,482, filed Sep. 19, 1988.

FIELD OF THE INVENTION

The present invention relates generally to a T cell growth factor. More particularly, the present invention relates to a mammalian T cell growth factor which is a glycoprotein capable of supporting interleukin 2- and interleukin 4-independent growth of helper T cells. This factor is further capable of augmenting proliferation if IL3- and IL4-responsive cells. Even more particularly, the present invention relates to the helper T cell growth factor P40, pharmaceutical compositions thereof and antibodies thereto. The present invention also contemplates a method for inducing the proliferation of helper T cells as well as IL3- and IL4-responsive cells. The helper T cell growth factor contemplated herein is useful in the stimulation of specific cells in the immune system.

BACKGROUND OF THE INVENTION

Many cytokines are polypeptides which directly or indirectly mediate host defense mechanisms and/or which mediate tissue growth differentiation. Cytokines have been recognized which mediate host defense against cancer and/or infection. Such cytokines include the interferons (IFN-$\alpha$, IFN-$\beta$ and IFN-$\gamma$), tumor necrosis factor (TNF-$\alpha$), lymphotoxin (TNF-$\beta$), the interleukins (IL1, 2, 3, 4, 5 and 6), leukoregulin, natural killer cell cytotoxic factor (NKCF), transforming growth factor (TGF), colony stimulating factors (CSF) such as macrophage (M-CSF), granulocyte (G-CSF) and macrophage, granulocyte-CSF (G,M-CSF) and oncostatin M. Each of the aforementioned cytokines have unique characteristics and a unique range of antiproliferative, cytostatic, antiviral or growth regulatory activity.

Several cytokines are synthesized by leukocytes, commonly in response to stimulation by microorganisms, antigens or mitogens. This has been observed in vitro. Following this stimulation in cell culture, the supernatant fluid is retrieved and cytokine activity identified, isolated and further characterized. In recent years, it has become increasingly clear that IL2 is not the only factor controlling T cell growth. Indeed, several cytokines, including IL4 (Fernandez-Botran et al., *Proc. Natl. Acad. Sci. USA*, 83; 9689-9693, 1986; Lichtman et al., *Proc. Natl. Acad. Sci. USA*, 84: 4293-4297, 1987), G,M-CSF (Woods et al., *J. Immunol.*, 138: 4293-4297, 1987; Kupper et al., *J. Immunol.*, 138, 4288-4292, 1987) and, in human system, the combination of IL1 and IL6 (Houssiau et al., *Eur. J. Immunol.* 18: 653-656, 1988), have now been shown to induce IL2-independent T cell proliferations. Consequently, the regulation of T cell growth is more complex than originally thought, although IL2 is a potent and broadly active T cell growth factor.

An important subset of T cells is the helper T cell ($T_H$). At least two types of helper T cells have been identified on the basis of functional criteria. One type of $T_H$ cell ($T_H1$) helps B cells in a linked, antigen-specific manner, and is required early in the response. Another type of $T_H2$) helps B cells in a nonlinked manner and is required later in the response.

Several years ago, a collection of helper T cell lines from lymph nodes of antigen-primed mice was obtained using the procedure described by Corradin et al., *J. Immunol.*, 119: 1048-1053, 1977. These cell lines were initiated by culture in the presence of antigen and were subsequently maintained, without addition of exogenous growth factors, by regular feeding with antigen and irradiated splenic antigen-presenting cells. Most of these cells produce large amounts of IL3, IL4, IL5 and IL6, but no IL2 and, therefore, belong to the $T_H2$ type defined by Mosmann et al., *J. Immunol.*, 136: 2348-2357, 1986.

In accordance with the present invention, it is surprisingly discovered that two clones derived from the above-mentioned cell lines proliferated in response to their own conditioned medium in the absence of antigen and feeder cells. The subject invention relates to a novel T cell growth factor distinct from other known cytokines. The new growth factor is useful as a therapeutic compound to stimulate proliferation of helper T cells.

SUMMARY OF THE INVENTION

The present invention is directed to a mammalian T cell growth factor which supports interleukin 2-independent and interleukin 4-independent growth of helper T cells, and is preferably obtained from mouse or human sources.

More preferably, this T cell growth factor is a protein having the identifiable characteristics of P40, derivatives or fragments thereof and the further capability of augmenting proliferation and IL3- and IL4-responsive cells. Methods of isolating P40, its derivatives and fragments are also provided.

Another aspect of the present invention relates to a pharmaceutical composition comprising an effective amount of P40, a derivative or fragment thereof and a pharmaceutically acceptable carrier useful in the stimulation of specific cells in the immune system. Optionally, these compositions may also contain IL3 or IL4.

Still another aspect of the present invention relates to antibodies specific to P40, an antigenic derivative or an antigenic fragment thereof useful in diagnostic assays for P40.

Yet another aspect of the present invention relates to a recombinant DNA molecule and expression vectors encoding the polypeptide portion of mammalian P40, a derivative or a fragment thereof, thereby providing a convenient source of recombinant P40.

Still yet another aspect of the present invention contemplates a method of proliferating helper T cells which comprises incubating said cells with a proliferating effective amount of P40 or a derivative thereof for a time and under conditions sufficient for said cells to proliferate.

A still further aspect of this invention relates to a method of proliferating IL3- or IL4-responsive cells by administering a combination of P40 and IL3 or IL4 to a mammal, especially a human, for a time and under conditions sufficient to stimulate said cells to proliferate.

BRIEF DESCRIPTION OF THE FIGURES

FIGS. 4A-4B illustrates the purity of P40 and its extent of glycosylation. Panel A is a photograph showing silver-stained NaDodSO4/PAGE of purified P40. The sample is run under reducing conditions. Panel B is an autoradiograph of $^{125}$I-P40 treated with various glycosylases. Mr of standards if given in kDa.

FIG. 7 shows the amino acid sequence of murine P40 obtained by chemical sequencing and the various peptides used in obtaining this sequence.

DETAILED DESCRIPTION OF THE INVENTION

Figure 1:
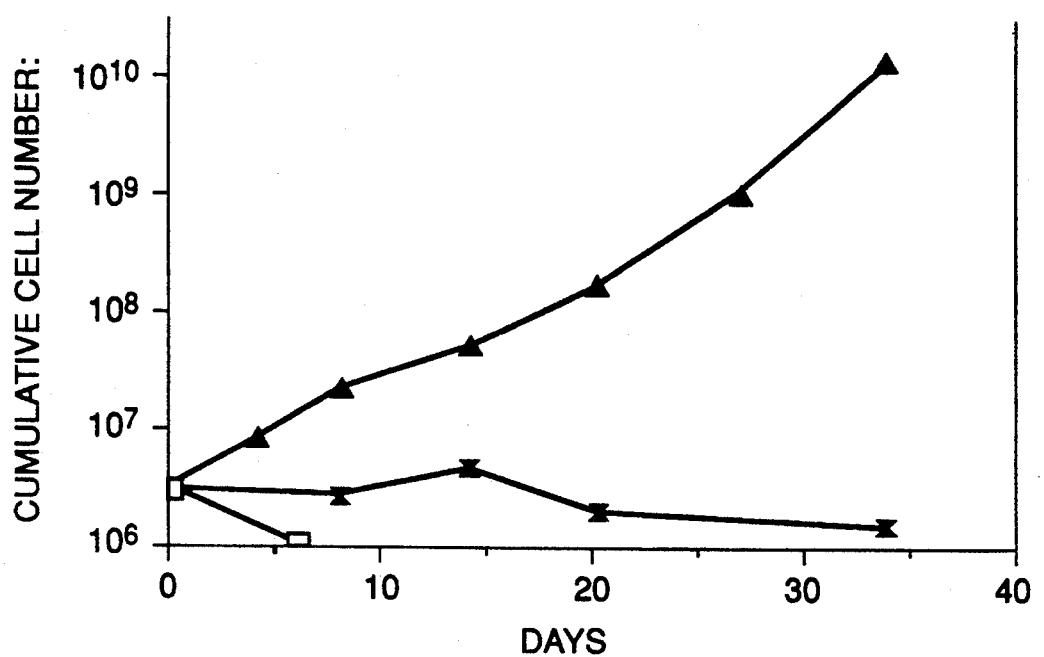
FIG. 1 is a graphical representation depicting long-term antigen-independent T cell growth induced by helper T cell supernatant (SN). TUC2.15 cells are grown without feeder cells and antigen in normal medium (□), in medium supplemented with IL2 (20 U/ml, ■) or with TUC2.15 SN (5% v/v, ▲).

The present invention relates to a mammalian T cell growth factor which comprises a protein which supports, or is capable of supporting, interleukin 2 (IL2)-independent and interleukin 4(IL4)-independent growth of helper T cells in the absence of antigen. In accordance with the present invention and using the methods contained herein, said T cell growth factor is biologically pure. By biologically pure is meant a composition comprising said T cell growth factor. The composition may comprise homogeneous T cell growth factor or may consist essentially of T cell growth factor. As used in the specification and appended claims, supporting IL2-independent and IL4-independent growth of helper T cells refers to the ability for said cells to proliferate in the absence of IL2 and/or IL4. This feature distinguishes the subject growth factor from others presently known. In accordance with the present invention, this ability is due to a novel and heretofore unknown T cell growth factor. Hereinafter, said growth factor is referred to as P40. As defined herein, derivatives of P40 encompass synthetic and naturally occurring amino acid substitutions, deletions and/or insertions as will be apparent to the skilled artisan. For example, non-essential amino acid deletions, i.e., deletion of amino acids which do not affect the activity of P40 are obtainable by genetic engineering means.

Furthermore, fragments of P40 are contemplated by the present invention. These fragments are peptides obtained from the P40 protein and may be prepared by proteolysis of purified P40. The peptides are purified by conventional means such as HPLC chromatography and the like, and are useful in determining the P40 amino acid sequence in preparing antibodies to specific domains of P40 and in identifying the P40 domains involved in stimulating T cell growth.

An antigenic derivative of P40 is defined to be a portion of P40 which is capable of reacting with an antibody specific to P40. All such derivatives are encompassed by the subject invention.

Accordingly, P40 is a protein, and more particularly, a glycoprotein, capable of supporting long-term IL2-independent and IL4-independent growth of helper T cell lines in the absence of antigen, and is isolated from helper T cell lines, especially mammalian lines like murine and human helper T cell lines. P40 is functionally distinct from all known interleukins and colony-stimulating factors. P40 is purified from the supernatant (SN) of lectin-stimulated mouse helper T cell lines to a specific activity of from about 10 U/mg to about $10^{10}$ U/mg, but generally to about $10^8$ U/mg and characterized as a basic (pI 10 for murine P40) single chain protein with a Mr of from about 30 to about 40 kDa.

P40 can be purified from the supernatant fluid of antigen stimulated mouse helper T cell clones (TUC2.15 and TUC7.51). Briefly, the supernatant fluid is concentrated and applied to a TSK-Phenyl chromatography column. Fractions with growth factor activity on factor-dependent TS1 cells are pooled, further fractionated on a Mono-Q chromatography column, and the resulting active fractions applied to a C1 reversed-phase HPLC column. Pure murine P40 is eluted at a concentration of about 35% acetonitrile.

Two observations indicate that P40 is a glycoprotein: (1) its heterogeneous migration pattern in NaDodSO4/PAGE and (ii) its binding to lentil lectin, which points to the presence of N-linked carbohydrate side chains. Consistent with this observation, a number of potential N-glycosylation sites (Asn-X-Thr motif) have been identified in the protein sequence determination. Moreover, additional evidence for extensive glycosylation of the molecule is obtained in experiments with N-glycanase treatment, which reduced the Mr of P40 to about 15 kDa. P40 is a stable molecule whose biological activity is not altered after exposure to NaDodSO4, acid pH or acetonitrile. By contrast, its activity is destroyed by 2-mercaptoethanol, which suggests that intramolecular disulfide bridges play an important role in maintaining appropriate folding of the molecule. P40 is also distinguished from known proteins on the basis of its complete amino acid sequence. The DNA and amino acid sequence of murine P40 and human P40 are described herein and indicate that the two proteins are 55% homologous.

In addition to the aforementioned distinguishing structural characteristics of P40, it also differs functionally from IL2. P40 is completely inactive on cytolytic T cell clones under conditions where there response to IL2 is very strong; conversely, IL2 fails to support long-term antigen independent growth of helper T cell lines, whereas P40 is very active in this system. To date, long-term growth of helper cells in response to P40 means greater than two months and may be indefinite. In contrast with these differences, a correlation is observed between the sensitivity of helper T cell lines to P40 and IL4, indicating that T cell activation by these two molecules is similarly regulated. However, the range of activities of IL4, which also stimulates the growth of a variety of IL3-dependent cell lines and of cytolytic T cells (Mosmann et al., *Proc. Natl. Acad. Sci. USA*, 83: 5654-5658, 1986; Widmer et al., *Nature*, 326: 795-798, 1987) is broader than that of P40, indicating that the functional overlap between the two factors, IL4 and P40, is only partial.

Another advantage of the subject T cell growth factor, P40, is the surprising discovery that P40 is specific for helper T cell lines. This indicates the existence of a growth-stimulatory mechanism restricted to the helper T cell subset. Such a mechanism is important for maintaining the balance between the supply of helper T cell products like IL2 and IL4 and their increased consumption by other lymphocytes activated in the course of the immune response.

While investigating the range of P40 activity, it was surprisingly discovered that P40 augments proliferation of IL3- or IL4-responsive cells in a synergistic manner. As used herein, IL3- and IL4-responsive cells are immune system cells which proliferate in response to IL3 or IL4, respectively. These cells may include IL3-dependent cells or IL4-dependent cells, but are not limited thereto. IL3-responsive cells include helper T cells, stem cells, mast cells, eosinophils, neutrophils, monocytes, megakaryocytes, basophils and erythropoid cells. IL4-responsive cells include helper T cells, activated cytotoxic T cells, macrophages, mast cells and B cells (Smith, K. A., *Biotechnology*, 7: 661-667, 1989).

Hence there is a strong synergism with respect to growth for cells stimulated with P40 and IL3, or P40 and IL4. In a thymidine uptake assay which measures cellular proliferation, the combination of cytokines P40 and IL3, or P40 and IL4, can stimulate thymidine uptake by a factor ranging from about 4 to 40 above the stimulatory effect of any one of the cytokines. In general, the synergism between P40 and IL3, or P40 and IL4, is dose dependent and cell line dependent. For these proteins and a given cell line, suboptimal doses of P40 range from about 1-25% of optimal P40 doses, suboptimal doses of IL4 range from about 5-30% of optimal IL4 doses, and close to optimal doses of Il3 range from about 70-100% of optimal IL3 doses. This synergism provides a further method to stimulate proliferation of IL3- and IL4-responsive cells, especially helper T cells, and is therapeutically useful in treating immune deficiencies, especially those diseases or disease states which benefit from proliferation of specific immune cells such as AIDS, or even from general proliferation of immune cells.

It is within the scope of the present invention to include biologically pure P40 in addition to homogeneous and heterogeneous compositions thereof. Thus in accordance with the present invention, supernatant (SN) from a helper T cell line not requiring antigen or feeders comprises P40. This SN is able to induce cell proliferation without further requirement for antigen or feeder cells. As further described in Example 1, the proliferation activity is not inhibited by either anti-IL4 or anti-IL2 receptor antibodies, indicating that said activity is mediated neither directly nor indirectly by these molecules. The active ingredient in the aforementioned SN is shown to be, in accordance with the present invention, P40. The SN is active on the test cells, TS1, inducing half-maximal proliferation at dilutions ranging of from about $10^{-6}$ to about $10^{-2}$ (v/v), and generally ranging of from about $10^{-5}$ to about $10^{-4}$ (v/v). Accordingly, in accordance with the present invention, the novel T cell growth factor P40 is active in biologically pure form and in homogeneous and heterogeneous compositions. As exemplified herein, SN fluid is in a form of heterogeneous composition of P40. Homogeneous compositions are exemplified herein to include pharmaceutical compositions containing homogeneous preparations of P40, its active derivatives or fragments, and the like.

The T cell growth factor P40 is contemplated herein to be useful in stimulating the proliferation of T helper cells in mammals. In a preferred embodiment, P40 is particularly useful in stimulating certain subsets of T helper cells in mammals. Accordingly, P40 is a new and useful therapeutic compound capable of stimulating specific cells within the immune cells. For example, this is particularly important for human patients carrying defects in certain subsets of T helper cells as may be the case with various AIDS patients or immune compromised patients. It should also be noted that of the many advantages of the present invention, the proliferation of helper T cells by P40 will have the additional effect of allowing increased amounts of other cytokines to be produced. Accordingly, the present invention also contemplates a method of treatment of immune deficiency comprising the administration of a proliferating effective amount of P40, an active derivative, or an active fragment thereof, for a time and under conditions sufficient to effect proliferation of helper T cells. In accordance with the present invention, the time required for the proliferation of helper T cell ranges from about two days to about seven days.

Accordingly, the subject invention contemplates a method for inducing and maintaining the proliferation of helper T cells, and preferably, certain subsets thereof, in a mammal which comprises administering to said mammal a proliferating-effective amount of a pharmaceutical composition containing P40, an active derivative or fragment thereof, for a time and under conditions sufficient for said cells to proliferate. Additionally, a method for inducing and maintaining the proliferation of helper T cells, and preferably certain subsets thereof, in a mammal, is contemplated by this invention in which a nucleic acid molecule encoding P40 is introduced into a T cell in such a manner that said nucleic acid molecule is expressed intracellularly, but extrachromosomally of said cell or following integration into a genome of said cell. In this case, the nucleic acid molecule is carried to said T cell and transferred into said cell by a second nucleic acid molecule (e.g., various viruses). The first nucleic acid molecule is manipulated such that it contains the appropriate signals for expression. That is, in accordance with the present invention, a method for proliferating T helper cells in a mammal is contemplated comprising administering a first nucleic acid molecule encoding P40, said nucleic acid molecule being contained in a pharmaceutically acceptable second nucleic acid carrier molecule such that said first nucleic acid molecule enters a T cell and is either maintained extrachromosomally or integrates into the genome of said target all in such a manner that said first nucleic acid molecule is expressed so as to produce an effective amount of P40. By nucleic acid molecule is meant the nucleotide sequence which encodes, directly or indirectly, P40 or a derivative thereof. A nucleic acid molecule is defined herein to mean RNA or DNA.

The active ingredients of a pharmaceutical composition comprising P40 are contemplated to exhibit excellent and effective therapeutic activity, for example, in the treatment of immune compromised diseases in mammals. Thus the active ingredients of the therapeutic compositions comprising P40 exhibit helper T cell proliferative activity when administered in therapeutic amounts which depend on the particular disease. For example, from about 0.5 $\mu$g to about 2000 mg per kilogram of body weight per day may be administered. The dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as by the oral, intraveneous (where water soluble), intramuscular, subcutaneous, intranasal, intradermal or suppository routes. Depending on the route of administration, the active ingredients which comprise P40 may be required to be coated in a material to protect said ingredients from the action of enzymes, acids and other natural conditions which may inactivate said ingredients. For example, the low lipophilicity of P40 may allow it to be destroyed in the gastrointestinal tract by enzymes capable of cleaving peptide bonds and in the stomach by acid hydrolysis. In order to administer P40 by other than parenteral administration, P40 should be coated by, or adminstered with, a material to prevent its inactivation. For example, P40 may be administered in an adjuvant, co-administered with enzyme inhibitors or in liposomes. Adjuvants contemplated herein include resorcinols, nonionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water P40 emulsions as well as conventional liposomes.

The active compounds may also be administered parenterally or intraperitoneally. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporoaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredient from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof.

When P40 is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 10 $\mu$g and 1000 $\mu$g of active compound.

The tablets, troches, pills, capsules, and the like, may also contain the following: a binder such as gum gragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 10 $\mu$g to about 2000 mg/ml of carrier. In the case of compositions containing supplementary active ingredients, the dosages are determined by reference to the usual dose and manner of administration of the said ingredients.

As used herein "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

A further aspect of this invention contemplates the use of P40 with IL3 or IL4 in a method to stimulate proliferation of IL3- or IL4-responsive cells and in a method of treatment of immune deficiency. Such methods are practiced in accordance with the therapeutic methods involving only P40 and as described herein. Likewise, pharmaceutical compositions containing P40 and IL3, or P40 and IL4 are provided in accordance with those which contain P40 alone. Further in this regard, IL3 and IL4 are commercially available and are used in therapeutically effective amounts. Pharmaceutically effective amounts of P40 when used in conjunction with IL3 or IL4 are the same as when P40 is used alone. Likewise, pharmaceutically effective amounts of IL3 or IL4 amounts can be similar to those provided for P40 alone. Preferred compositions of P40 and IL3 according to the present invention are prepared so that a unit dosage form contains each protein in an amount ranging from about 0.5 $\mu$g to about 2000 mg. Preferred compositions of P40 and IL4 are likewise prepared so that a unit dosage form contains each protein in an amount ranging from about 0.5 $\mu$g to about 2000 mg. In these compositions, the relative amount of P40 to IL3 or IL4 can be varied or the same.

The present invention also relates to antibodies to P40, its derivatives or fragments. Such antibodies are contemplated to be useful in developing detection assays (immunoassays) for P40, especially during the monitoring of a therapeutic regiment and in the purification of P40. The antibodies may be monoclonal or polyclonal. Additionally, it is within the scope of this invention to include any second antibodies (monoclonal or polyclonal) directed to the first antibodies discussed above. The present invention further contemplates use of these second antibodies in detection assays and, for example, in monitoring the effect of an adminstered pharmaceutical preparation. Furthermore, it is within the scope of the present invention to include antibodies to the glycosylated regions of P40, and to any molecules complexed with said P40. Accordingly, in accordance with this invention, an antibody to P40 encompasses antibodies to P40, or antigenic parts thereof, and to any associated molecules (e.g., glycosylated regions, lipid regions, carrier molecules, and the like).

The P40, or parts thereof, considered herein are purified, as exemplified in Example 3, then utilized in antibody production. Both polyclonal and monoclonal antibodies are obtainable by immunization with P40, its derivatives, polypeptides or fragments, and either type is utilizable for immunoassays. The methods of obtaining both types of sera are well known in the art. Polyclonal sera are less preferred, but are relatively easily prepared by injection of a suitable laboratory animal with an effective amount of the purified P40, or parts thereof, collecting serum from the animal and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in the present immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard, J. Y. and Hoffman, T., "Basic Facts About Hybridomas," in *Compendium of Immunology*, vol. II, L. Schwartz (Ed.) (1981); Kohler, G. and Milstein, C., *Nature*, 256:495–497 (1975); *European Journal of Immunology*, 6: 511–519 (1976), Koprowski et al., U.S. Pat. No. 4,172,124, Koprowski et al., U.S. Pat. No. 4,196,265 and Wands, U.S. Pat. No. 4,271,145, the teachings of which are herein incorporated by reference.

Unlike preparation of polyclonal sera, the choice of animal for monoclonal antibody production is dependent on the availability of appropriate immortal lines capable of fusing with lymphocytes thereof. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with from about 1 mg to about 20 mg of the purified P40 or parts thereof. Usually the injecting material is emulsified in Freund's complete adjuvant. Boosting injections may also be required. The detection of antibody production can be carried out by testing the antisera with appropriately labeled antigen. Lymphocytes can be obtained by removing the spleen or lymph nodes of sensitized animals in a sterile fashion and carrying out fusion. Alternatively, lymphcytes can be stimulated or immunized in vitro, as described, for example, in C. Reading, *J. Immunol. Meth.*, 53: 261-291, 1982.

A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: $MPC_{11}$-X45-6TG, P3-NS1-1-Ag4-1. P3-X63-Ag8, or mutants thereof such as X63-Ag8.653, SP2-0-Ag14 (all BALB/C derived), Y3-'Ag1.2.3 (rat) and U266 (human).

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1000 to 6000. It gives best results when diluted to about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion gives optimum results. The ratio between lymphocytes and malignant cells is optimized to avoid cell fusion among spleen cells and a range of from about 1:1 to about 1:10 gives good results.

The successfully fused cells can be separated from the myeloma line by any technique known by the art. The most common and preferred method is to choose a malignant line which is Hypoxanthine Guanine Phosphoribosyl Transferase (HGPRT) deficient, which will not grow in an aminopterin-containing medium used to allow only growth of hybrids and which is generally composed of hypoxanthine $1.10^{-4}M$, aminopterin $1\times10^{-5}M$ and thymidien $3\times10^{-5}M$, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation. Detection of hybridoma antibodies scan be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21-23 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies form the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8-12 days after intraperitoneal injection. The ascites contain a higher concentration of antibodies but include both monoclonals and immunoglobulines from the inflammatory ascites. Antibody purification may then be achieved by, for example, affinity chromatography.

The presence of P40 contemplated herein, or antibodies specific for same, in a patient's serum, tissue or tissue extract, can be detected utilizing antibodies prepared as above, either monoclonal or polyclonal, in virtually any type of immonoassay. A wide range of immunoassay techniques are available as can be seen by reference to U.S. Pat. Nos. 4,016,043; 4,424,279 and 4,018,653. This, of course, includes both single-site and two-site, or "sandwich", assays of the non-competitive types, as well as in the traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen secondary complex, a second antibody, labeled with a reporter molecule capable of producing a detectable signal is then added and incubated, allowing time sufficient for the formation of a tertiary complex of antibody-antigen-labeled antibody (e.g., antibody-P40-antibody). Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody, or a reverse assay in which the labeled antibody and sample to be tested are first combined incubated and then added to the unlabeled surface bound antibody. These techniques are well known to those skilled in the art, and then possibly of minor variations will be readily apparent.

In the typical forward sandwich assay, a first antibody having specificity for P40, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking, covalently binding or physically absorbing the molecule to the insoluble carrier. Following binding, the polymer-antibody complex is washed in preparation for the test sample. An aliqout of the sample to be tested is then added to the solid phase complex and incubated at 25° C. for a period of time sufficient to allow binding of any subunit present in the antibody. The incubation period will vary but will generally be in the range of about 2-40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten. By "reporter molecule", as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymers, fluorophores or radionuclide containing molecules (i.e., radioisotopes). In the case of an enzyme imunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, $\beta$-galactosidase and alkaline phosphatase, among other. The substrates to be used with the specific enzymes are generally chosed for the production, upon hydrolysis by the corresponding enzyme, of a detectable color change. For example, p-nitrophenyl phosphate is suitable for the use with alkaline phosphatase conjugates; for peroxidase conjugates, 1,2-phenylenediamine, 5-aminosalicyclic acid, or tolidine, are commonly used. It is also possible to employ fluorogenic substrates, which yield a fluorescent product rather than the chromogenic substrates noted above. In all cases, the enzyme-labeled antibody is added to the first antibody hapten complex, allowed to bind, and then to the first antibody hapten complex, allowed to bind, and then the excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to detect directly or indirectly (i.e., via antibodies) the P40 of this invention.

Accordingly, the present invention is also directed to a kit for the rapid and convenient assay of P40 in mammalian body fluids (e.g. serum, tissue extracts, tissue fluids), in vitro cell culture supernatants, and cell lysates. The kit is compartmentalized to receive a first container adapted to contain an antibody to P40, or to an antigenic component thereof, and a second container adapted to contain a second antibody to P40, or to an antigenic component thereof, said second antibody being labeled with a reporter molecule capable of giving a detectable signal as hereinbefore described. If the reporter molecule is an enzyme, then a third container adapted to contain a substrate for said enzyme is provided. In an exemplified use of the subject kit, a sample to be tested for P40 is contacted with the contents of the first container for a time and under conditions for P40, if present, to bind to the antibodies contained in said first container. After removal of unbound material (e.g. by washing with sterile phosphate buffered saline) the secondary complex is contacted with the contents of the second container. If the antibodies of the first container have bound to P40, then the antibodies of the second container bind to the secondary complex to form a tertiary complex and, since said second antibodies are labeled with a reporter molecule, when subjected to a detecting means, the tertiary complex is detected.

Another aspect of this invention relates to a recombinant nucleic acid or an isolated nucleic acid molecule, said molecule defined herein to be DNA or RNA, encoding P40 or parts thereof. In one embodiment the recombinant nucleic acid molecule is complementary DNA (cDNA). It is considered within the scope of the present invention to include the cDNA molecule encoding mammalian P40, preferably murine and human P40, or to regions or parts thereof including any base deletion, insertion or substitution or any other alteration with respect to nucleotide sequence or chemical composition (e.g. methylation and glycosylation). P40 encoded by cDNA is referred to herein as recombinant P40. Moreover, another embodiment of this invention is directed to the genomic P40 gene, which may include recombinant clones like cosmides encoding the entire gene or subclones encoding exons, introns or any region of the mammalian P40 gene. Recombinant DNA encoding such subregions of the gene are useful as hybridization probes to detect the presence of P40 genes.

Methods considered useful in obtaining recombinant P40 cDNA are contained in Maniatis et al., 1982, in *Molecular Cloning: A Laboratory Manual,* Cold Spring Harbor Laboratory, New York, pp. 1-545, for example, or any of the myriad of laboratory manuals on recombinant DNA technology which are widely available. Briefly, polyadenylated mRNA is obtained from stimulated helpter T cells and fractionated on agarose gels. Optionally, aliquots of mRNA can be injected into *Xenopus laevis* oocytes for translation and assayed for P40 activity using the methods contained herein to enriched fractions of mRNA translating into P40 active molecules. Alternatively, mRNA not enriched is used as template for cDNA synthesis. Libraries of cDNA clones are constructed in the Pst1 site of the vector pBR322 (using homopolymer tailing) or in a variety of other vectors (e.g. the Okayama-Berg cDNA cloning vectors, Messing cDNA cloning vectors and the like).

Specific cDNA molecules in a vector in said library is then selected by using specific oligonucleotides designed, based on amino acid sequences contained within P40, to encode at least part of said sequence. Particularly useful is the internal, partial amino acid sequence of murine P40 obtained after cyanogen bromide treatment which comprises:

NH₂—Ala Gly Asn Thr Leu Ser Phe Leu Lys Ser Leu Leu Gly Thr Phe Gln Lys Thr Glu.

Oligonucleotide sequences based on the foregoing amino acid sequence are particularly useful in identifying cDNA clones encoding P40 or its derivatives. Thus, poly(A)⁺RNA can be prepared from the murine helper T cell line TUC7.51 after 24 hours stimulation with Concanavalin A (Con A) and used as a template for cDNA synthesis. The cDNA can be cloned into BamHI site of a pUC8 vector, transformed into *E. coli* and screened using a 64-fold degenerate probe corresponding to the amino acid sequence FQKTEMQ and subsequently with a 128-fold degenerate probe corresponding to the amino acid sequence ENLKDDP (see Example 9 for the exact sequence of the probes). The resulting positive clones are useful to isolate other mammalian genomic P40 genes and cDNAs. For example, the murine cDNA clone is used to screen a human genomic library, or other mammalian genomic library, to identify either the entire genomic gene or at least an exon thereof. If only a portion of the gene is isolated by this method, the remainder of the gene can be isolated by "chromosomal walking" with the new clone. Further, a genomic clone is particularly useful to isolate a cDNA clone and vice versa, especially from the same species. Thus, the murine cDNA clone is used to isolate the murine genomic P40 gene.

The cDNA sequence encoding murine P40 is set forth below with the corresponding amino acid sequence:

```
                    -18                         -10
            Met Leu Val Thr Tyr Ile Leu Ala Ser Val Leu Leu Phe Ser Ser
5'CAGACTCCCGTCAACATGTTGGTGACATACATCCTTGCCTCTGTTTTGCTCTTCAGTTCT 1                                    10
Val Leu Gly Gln Arg Cys  Ser Thr Thr Trp Gly Ile Arg Asp Thr Asn Tyr Leu Ile Glu
GTGCTGGGCCAGAGA TGC  AGCACCACATGGGGCATCAGAGACACCAATTACCTTATTGAA
                                                                 100

20                                            30
Asn Leu Lys Asp Asp Pro Pro Ser Lys Cys  Ser Cys  Ser Gly Asn Val Thr Ser Cys  Leu
AATCTGAAGGATGATCCACCGTCAAAA TGC AGC TGC AGCGGCAACGTGACCAGC TGC TTG 40                                      50
Cys  Leu Ser Val Pro Thr Asp Asp Cys  Thr Thr Pro Cys  Tyr Arg Glu Gly Leu Leu Gln
TGT CTCTCCGTCCCAACTGATGAT TGT ACCACACCG TGC TACAGGGAGGGACTGTTACAG
                          200

60                                       70
Leu Thr Asn Ala Thr Gln Lys Ser Arg Leu Leu Pro Val Phe His Arg Val Lys Arg Ile
CTGACCAATGCCACACAGAAATCAAGACTCTTGCCTGTTTTCCATCGGGTGAAAAGGATA
                                                                 300

80                                     90
Val Glu Val Leu Lys Asn Ile Thr Cys  Pro Ser Phe Ser Cys  Glu Lys Pro Cys  Asn Gln
GTTGAAGTCCTAAAGAACATCACG TGT CCGTCCTTTTCC TGC GAAAAGCCA TGC AACCAG 100                                       110
Thr Met Ala Gly Asn Thr Leu Ser Phe Leu Lys Ser Leu Leu Gly Thr Phe Gln Lys Thr
ACCATGGCAGGCAACACACTGTCATTTCTGAAGAGTCTCCTGGGGACGTTCCAGAAGACA
                                                                 400

120                    126
Glu Met Gln Arg Gln Lys Ser Arg Pro
GAGATGCAAAGGCAGAAAAGCCGACCATGAAGACAGATGCTATTTATTCTATTTATTGAA

TTTACAAAACCTCCCCTCCTTAACTGTTACAGTGAAGAAATAAACTAAGCTATTCT3'
                                  500
```

The cDNA sequence with the corresponding amino acid sequence of human P40 is set forth below:

```
            -18
        MET LEU LEU ALA MET VAL LEU THR SER ALA LEU LEU LEU CYS SER VAL ALA
CCGCTGTCAAG ATG CTT CTG GCC ATG GTC CTT ACC TCT GCC CTG CTC CTG TGC TCC GTG GCA  62

1                                       10
GLY GLN GLY CYS PRO THR LEU ALA GLY ILE LEU ASP ILE ASN PHE LEU ILE ASN LYS MET
GGC CAG GGG TGT CCA ACC TTG GCG GGG ATC CTG GAC ATC AAC TTC CTC ATC AAC AAG ATG 122

20                                      30
GLN GLU ASP PRO ALA SER LYS CYS HIS CYS SER ALA ASN VAL THR SER CYS LEU CYS LEU
CAG GAA GAT CCA GCT TCC AAG TGC CAC TGC AGT GCT AAT GTG ACC AGT TGT CTC TGT TTG 182
```

```
                40                                    50
            GLY ILE PRO SER ASP ASN CYS THR ARG PRO CYS PHE SER GLU ARG LEU SER GLN MET THR
            GGC ATT CCC TCT GAC AAC TGC ACC AGA CCA TGC TTC AGT GAG AGA CTG TCT CAG ATG ACC  242

60                                         70
            ASN THR THR MET GLN THR ARG TYR PRO LEU ILE PHE SER ARG VAL LYS LYS SER VAL GLU
            AAT ACC ACC ATG CAA ACA AGA TAC CCA CTG ATT TTC AGT CGG GTG AAA AAA TCA GTT GAA  302

90
            VAL LEU LYS ASN ASN LYS CYS PRO TYR PHE SER CYS GLU GLN PRO CYS ASN GLN THR THR
            GTA CTA AAG AAC AAC AAG TGT CCA TAT TTT TCC TGT GAA CAG CCA TGC AAC CAA ACC ACG  362

100                                        110
            ALA GLY ASN ALA LEU THR PHE LEU LYS SER LEU LEU GLU ILE PHE GLN LYS GLU LYS MET
            GCA GGC AAC GCG CTG ACA TTT CTG AAG AGT CTT CTG GAA ATT TTC CAG AAA GAA AAG ATG  422

126
            ARG GLY MET ARG GLY LYS ILE
            AGA GGG ATG AGA GGC AAG ATA TGAAGATGAAATATTATTTATCCTATTTATTAAATTTAAAAA  485
```

Once identified, cDNAs or recombinant DNAs encoding all or part of recombinant P40 are ligated into expression vectors. Additional genetic manipulation is routinely carried out to maximize expression of the cDNA in the particular host employed. Accordingly, P40 may be synthesized in vitro by inserting said cDNA sequence into a replicable expression vector, transforming the resulting recombinant molecule into a suitable host and then culturing or growing the transformed host under conditions requisite for the synthesis of the molecule. The recombinant molecule defined herein should comprise a nucleic acid sequence encoding a desired polypeptide inserted downstream of a promoter, a eukaryotic or prokaryotic replicon and a selectable marker such as resistance to an antibiotic.

A promoter consists of a specific nucleic acid sequence that is operably linked to the DNA encoding the desired polypeptide which is capable of effecting expression of said polypeptide. Likewise, the promoter can be replaced or augmented by any other genetic elements capable of effecting gene expression, including such elements as enhancers, transcription terminators, poly(A) signals and the like. The latter three elements are not always necessary and their use will depend on both the vector and host system used for gene expression. The need for any of these elements can be easily determined by one skilled in the art. Promoters are DNA sequence elements for controlling gene expression, in particular, they specify transcription initiation sites. Prokaryotic promoters that are useful include the lac promoter, the trp promoter, the $P_L$ and $P_R$ promoters of lambda and the T7 polymerase promoter. Eukaryotic promoters are especially useful in the invention and include promoters of viral origin, such as the SV40 late promoter and the Molony Leukemia Virus LTR, yeast promoters and any promoters or variations of promoters designed to control gene expression, including genetically-engineered promoters. Control of gene expression includes the ability to regulate a gene both positively and negatively (i.e., turning gene expression on or off) to obtain the desired level of expression.

One skilled in the art has available many choices or replicable expression vectors, compatible hosts and well-known methods for making and using the vectors. Recombinant DNA methods are found in any of the myriad of standard laboratory manuals on genetic engineering.

The recombinant molecule may also require a signal sequence to facilitate transport of the synthesized polypeptide to the extracellular environment. Alternatively, the polypeptide may be retrieved by first lysing the host cell by a variety of techniques such as sonication, pressure dissintegration or toluene treatment. Hosts contemplated in accordance with the present invention can be selected from the group comprising prokaryotes (e.g., *Escherichia coli*, Bacillus sp., Pseudomonas sp.) and eukaryotes (e.g., mammalian cells, yeast and fungal cultures, insect cells and plant cultures). The artisan will also recognize that a given amino acid sequence can undergo deletions, substitutions and additions of nucleotides or triplet nucleotides (codons). Such variations are all considered within the scope of the present invention and may be prepared by site-directed mutagenesis technique. Additionally, depending on the host expressing recombinant P40, said P40 may or may not be glycosylated. Generally, eukaryotic cells, for example mammalian T cells and the like, provide glycosylated, recombinant P40. Prokaryotic cells, for example bacteria such as *Escherichia coli* and the like, do not glycosylate proteins. Hence, both glycosylated and non-glycosylated recombinant P40 are encompassed by the present invention.

Yet another aspect of the present invention provides transformant microorganisms and cultured cells containing the instant expression-vectors. Transformant microorganisms and cultured cells are made by introducing the replicable expression vector encoding mammalian P40, a derivative or a fragment thereof, into the desired cell or microorganisms by transformation or transfection or infection of virus or bacteriophage particles. Processes for transformation are well-known in the art and include, but are not limited to $CaCl_2$ treatment and electroporation for bacterial cells and $CaPO_4$ coprecipitation, protoplast fusion and electroporation for eukaryotic cells. Direct infection can be used when the vectors are viruses or bacteriophages. The detailed methods for these techniques can be found in standard laboratory manuals on recombinant DNA technology. The invention further contemplates any method for incorporating DNA into a host organism.

Another aspect of the present invention relates to the helper T cell lines which produce P40. As defined herein, P40 or compositions comprising same, stimulate the development of permanent antigen-independent T helper cell lines which are maintained by subcultivation every 3 to 4 days in medium with P40. Even more particularly, the present invention is directed to TS1, one of the factor-dependent cell lines derived from TUC2.15.

The following examples further illustrate the present invention.

EXAMPLE 1

Materials and Methods

Medium

Dulbecco's modified Eagle's medium supplemented with 10% (v/v) fetal bovine serum (FCS), 50 μM β-mercaptoethanol, 0.55 mM L-arginine, 0.24 mM L-asparagine and 1.25 mM L-glutamine are used for most cell lines except for 7TD1 and BCL1 which are grown in Iscove's medium.

T Cell Clones and Lines

Helper T cell lines are established and maintained in the absence of exogenous growth factors as described by Van Snick et al. *Proc. Natl. Acad. Sci.* USA 83:9679-9683, 1986. Lines TUC2 and TUC7 are derived from C57BL/6 mice immunized with keyhole limpet hemocyanin. Line TUC5 is obtained from the same strain of mice but after immunization with human transferrin. TUC13 is an allospecific BALB/c anti-C57B/6 line. Individual clones are derived from these lines by limiting dilution in the presence of 10% (v/v) medium contained by rat spleen cells stimulated with concanavalin A, and are denoted TUCx.y (where x stands for the number of the line and y for the number of the clone). These clones are subsequently expanded and maintained without exogenous growth factors like the parental cell lines. Cytolytic T cell clones of DBA/2 origin directed against syngeneic P815 mastocytoma are maintained with 50% (v/v) mixed lymphocyte culture medium as described by Maryanski et al. *Eur. J. Immunol.* 12:401-406, 1982. For use in growth factor assays, the T cells are separated from feeder cells by centrifugation over a layer of Lymphoprep (Nycomed AS, Oslo, Norway) washed and incubated at $5 \times 10^4$ cells/well. Proliferations are measured on day 3 after a 6 hr pulse with methyl-labeled [$^3$H]-thymidine (0.5 μCi/well).

Preparation of Helper T Cell Supernatants

TUC2.15 and TUC7.51 cells, obtained from cultures stimulated 2 weeks earlier with antigen and feeder cells, are adjusted to $2 \times 10^6$ cells/ml and incubated for 2-3 days in medium containing 0.5% (v/v) FCS and concanavalin A (ConA, 5 μg/ml). Supernatants (SN) are collected by centrifugation at 10,000 g for 20 min. When used for culture, crude SN are supplemented with 0.1M methyl-α-D-mannoside.

TS1 Growth Factor Assay

Factor-dependent TS1 cells are cultured in 1% (v/v) TUC2.15 SN. Before use in the growth factor assay, the cells are washed free of SN and cultured at a density of $3 \times 10^3$ cells/well in 200 μl with serial dilutions of samples to be tested. After 3 days, cell growth is measured by colorimetric determination of hexosaminidase levels according to Landegren *J. Immunol. Methods* 67:379-388, 1984. The dilution giving half-maximal absorbance at 405 nm is arbitrarily assigned one U/ml of activity.

Other Cell Lines

CTLL-2 (Gillis et al., *J. Immunol.* 120:2027-2032, 1978) is grown with 100 U/ml of human recombinant IL-2 DA-1 (Ihle et al. *Adv. Viral Oncol.* 4:95-137, 1984), Ea3.15 (Palacios et al. *J. Exp. Med.* 152:1036-1047, 1980) with 10% (v/v) WEHI-3 SN as a source of IL3 and 7TD1 with a 1/500 dilution of TUC2.15 SN as a source of IL6 (Van Snick et al. supra). Assays using these cell lines are carried out as described for the TS1 line and proliferations are measured either by hexosaminidase determinations or by thymidine incorporation. In vivo passaged BCL1 cells (Slavin et al. *Nature* 272:624-626, 1978) are frozen in aliquots and thawed just before use. Proliferation of BCL1 is measured by thymidine incorporation in 7 day-old cultures seeded with $10^4$ cells/well.

Cytokines and Growth Factors

Purified natural human IL1β (Van Damme et al., *Nature* 314:266-268, 1985), recombinant human IL2 (Devos et al. *Nucl. Acids Res.* 11:4307-4323) and purified murine IL3 (Ihle et al. *J. Immunol.* 129:2431-2436, 1982) are as described. Human recombinant granulocyte colony-stimulating factor (G-SCF) and mouse recombinant granulocyte-macrophage colony stimulating factor (GM-CSF) is described by DeLamarter et al. *Embo J.* 4:2575-2581, 1985. Platelet-derived growth factor (PDGF) is described by Heldin et al. *Proc. Natl. Acad. Sci.* USA 76:3722-3726, 1979. Epidermal growth factor (EGF) is purchased from Boehringer Mannheim (Fed. Rep. Germany). Mouse IL4, IL5 and IL6 are purified as described by Van Snick, supra, and Vink et al. *Eur. J. Immunol.* 8:607-612, 1988.

Antibodies

Anti-IL4 antibody 11B11 (Ohara et al. *Nature* 315:333-336, 1985) and anti-IL2 receptor antibody 5A2 (Moreau et al. *Eur. J. Immunol.* 17:929-935, 1987) are as described.

Purification of TS1 Growth Factor

Adsorption to silicic acid and gel filtration is performed as described (Van Snick supra). Active fractions from the gel filtration column are pooled, concentrated by ultrafiltration on an Amicon YM-10 membrane in the presence of $10^{-4}$ (v/v) dilution of Tween 20 and transferred to 1M Na$_2$SO$_4$ buffered to pH 7.0 with 0.1M sodium phosphate before injection onto a TSK-Phenyl column (LKB, Bromma, Sweden) equilibrated in the same buffer. After a 10 min wash in the starting buffer, elution is carried out at 0.6 ml/min with a linear gradient of a 1:1 mixture of a sodium phosphate buffer (0.1M pH 7.0) and ethylene glycol. Active fractions are further fractionated on a MonoQ column (Pharmacia Fine Chemicals, Uppsala, Sweden) equilibrated in 20 m ethanolamine-HCl pH 9.5, 20 mM NaCl and $10^{-4}$ (v/v) Tween 20. The column is developed at 0.8 ml/min with a 30 min linear gradient of NaCl (8 mM/min). Pooled active fractions are concentrated and adjusted to contain 0.05% (w/v) trifluoroacetic acid (TFA) before injection on a Cl 25-nm pore-size TSK TMS-250 HPLC column (LKB). The column is developed for the first 10 min with a linear gradient from 0 to 35% (W/v) acetonitrile in 0.05% (w/v) TFA, which is followed by a shallow 35-36% gradient for the next 60 min. Flow rate is adjusted to 0.8 ml/min; 1 min fractions are collected in Eppendorf tubes containing 10 μl of 1M NH$_4$HCO$_3$ and 5 μl of Tween 20 (1% (v/v) in water) and lyophilised. Total protein is measured fluorometrically with benzoxanthene following Neuhoff et al. *Hoppe-Seyler's Z. Physiol. Chem.* 360:1657-1670, 1979. The purity of the final product is assessed by NaDodSO$_4$/PAGE in 12% (w/v) acrylamide gels. Isoelectric focusing is performed with a LKB (Bromma, Sweden) vertical gel apparatus. Material is recovered from gels by overnight incubation in 130 mM NaCl containing Tween 20 ($10^{-4}$ v/v) and 10 mM sodium phosphate pH7.0. Affinity chromatography on lentil lectin-Sepharose is done following the procedure described by the manufacturer (Pharmacia, Uppsala, Sweden).

Amino Acid Sequence Analysis

Automated amino acid sequence analysis is performed with an Applied Biosystems sequencer (model 477A) equipped with an on-line phenylthiohydranthoin amino acid analyzer (model 120A). In situ cyanogen bromide cleavage of P40 (~10 μg) is performed on the glass fiber sample disk of the gas-phase sequencer according to a procedure described by Simpson et al. Biochem. Internat. 8:787–791, 1984, hereinafter Simpson I. Sequence comparisons are made with the following databases: Protein Sequence database of PIR, National Biomedical Research Foundation (release 15.0, December 1987); Swiss-Port Protein Sequence Data Bank version 5 (September 1987, compiled by A. Bairoch, University of Geneva, Medical Biochemistru Department, 1211 Geneva 4, Switzerland); G.B. trans Protein Data Base Release 1.0 (August 1987) compiled from GENBANK release 50.0 by J. Coventry, Walter and Eliza Hall Institute of Medical Research, Parkville 3050 Australia; and PG trans Protein Data Base release 38.0 (December 1985) GENBANK, Instit. Pasteur, Paris, France.

EXAMPLE 2

Detection of T Cell Growth Factory Activity

TUC2.15 is a C57B1/6 helper T cell line that requires antigen and antigen-presenting cells for long term growth in vitro. In an attempt to grow these cells without feeders and antigens it is surprisingly discovered that, after supplementing the culture medium with 10% (v/v) autologous supernatant (SN) obtained after stimulation with ConA, this SN is able to induce cell proliferation without further requirement for antigen or feeder cells. This growth factor activity is not inhibited by either anti-IL4 or anti-IL2 receptor antibodies (Table 1), indicating that the activity is mediated neither directly nor indirectly by these molecules.

In addition to its activity in short term proliferations, the SN also readily stimulates the development of permanent antigen-independent cell lines, which are maintained by subcultivation every 3–4 days in medium supplemented with 1% (v/v) SN (FIG. 1). Attempts to derive antigen-indenpendent cells lines with IL2 in this manner are to date unsuccessful. A second helper T cell clone, TUC7.51 also gives rise to an antigen-independent cell line upon culture in autologous SN. The factors active on the two cell lines are apparently identical, since TUC7.51 SN supported the growth of TUC2.15 cells and vice versa.

TS1, one of the factor-dependent cell lines derived from TUC2.15 is selected for further identification of the growth factor. This choice is based on the observation that TS1 grows quickly, with a doubling time of 11 h, and responds to very small concentrations of SN, half-maximal proliferation being obtained at dilutions between $10^{-5}$ and $10^{-4}$ (v/v). To determine the specificity of the TS1 assay, cells are incubated with a variety of purified growth factors or crude SN and found that only IL4 and TUC2.15 SN support TS1 growth (Table 2). Since anti-IL4 antibodies fail to inhibit the effects of TUC2.15 SN, the aforementioned activity is a new T cell growth factor.

TABLE 1

Proliferation of TUC2.15 Helper T Cells Induced By Autologous Supernatant (SN); Independence from IL2 and IL4

| Antibodies Added | Proliferation in response to | | |
|---|---|---|---|
| | IL2 | IL4 | TUC2.15 SN |
| | (kepm) | | |
| none | 152 | 18 | 37 |
| anti-IL2 receptor | 4 | 16 | 32 |
| anti-IL4 | 156 | 1 | 33 |

TUC2.15 helper T cells ($5 \times 10^4$/well) are incubated for 3 days with IL2 (100 U/ml), IL4 (100 U/ml) or TUC2.15 SN (1% v/v) in the presence of anti-IL2 receptor antibody 5A2 (30 μg/ml) or anti-IL4 antibody 11B11 (10 μg/ml). Thymidine incorporation is measured on day 3.

TABLE 2

Growth of TS1 in Response to Various Cytokines

| Factors | Dose/Dilution | Cell Growth ($A^{405}$) |
|---|---|---|
| TUC2.15 SN | 1/12.500 | 1.96 |
| IL1 | 100 U/ml | 0 |
| IL2 | 100 U/ml | 0 |
| IL3 | 100 U/ml | 0.01 |
| IL4 | 100 U/ml | 1.36 |
| IL5 | 100 U/ml | 0 |
| IL6 | 20 ng/ml | 0 |
| GM-CSF | 10 ng/ml | 0 |
| G-CSF | 4 ng/ml | 0 |
| M-CSF (crude) | 1/4 | 0.02 |
| EGF | 50 ng/ml | 0 |
| PDGF | 4 ug/ml | 0.02 |

TS1 cells are incubated for 3 days in the presence of various factors or SN. All reagents are tested over a 100-fold range but results are given for the highest dose only. None of the factors that score negatively at the highest dose have any effect at lower does. Cell growth is measured by colorimetric determination of hexosaminidase levels. Absorbance (A) of cultures at 405 nm incubated without growth factors ranges from about 0.10 to about 0.15 and is subtracted.

EXAMPLE 3

Purification of the T Cell Growth Factor

Figure 2:
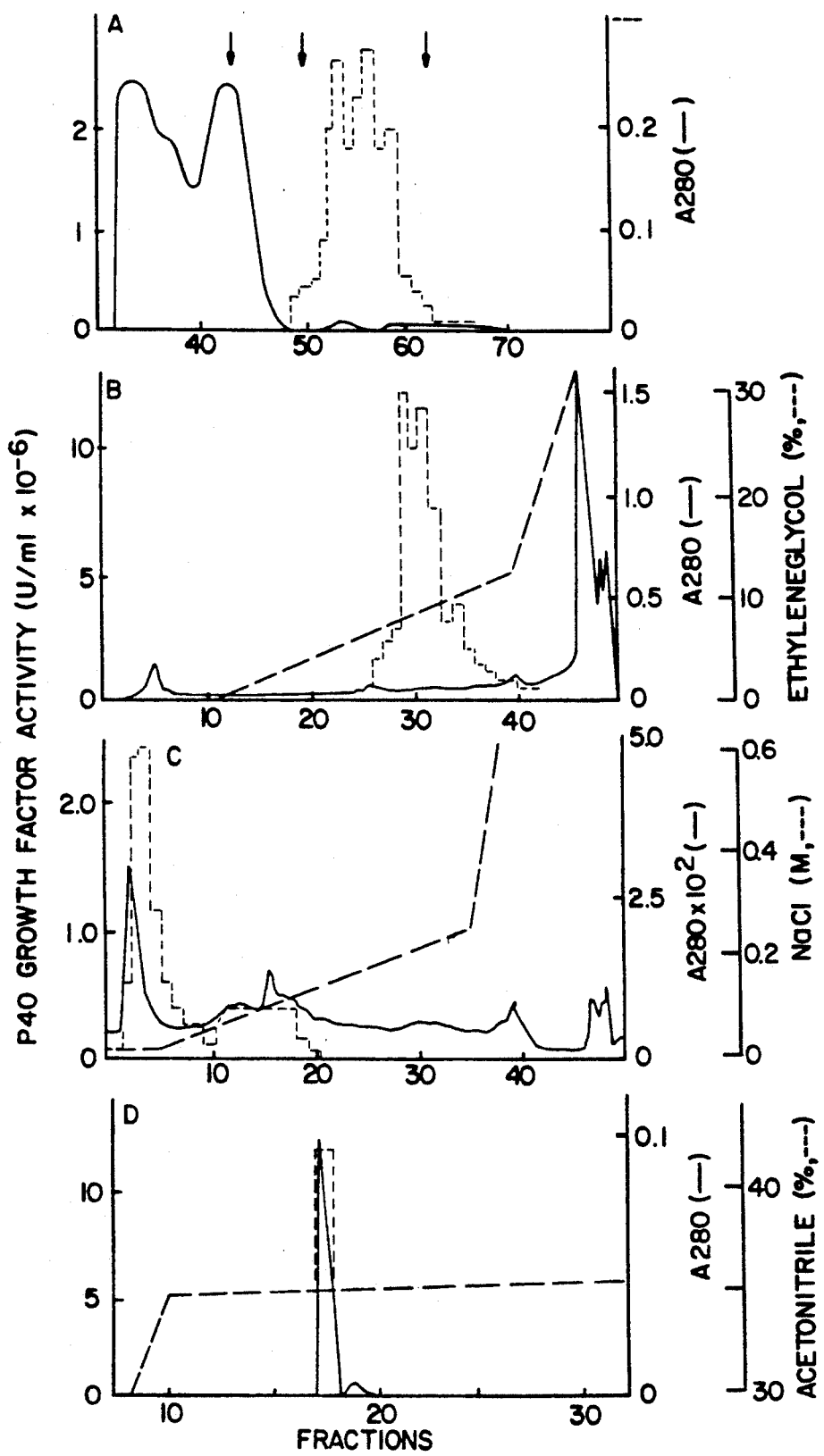
FIGS. 2A-2D is a graphical representation depicting purification of P40. TUC7.51 supernatant is fractioned sequentially on an Ultrogel AcA54 gel filtration column (A), a TSK-phenyl hydrophobic interaction column (B), a Mono-Q anion exchange column (C) and C1-reversed phase column (D). The shaded area represents P40 activity. Molecular mass standards shown in panel A are bovine serum albumin (BSA, 67 kDa), natural IL5 (45 kDa) and recombinant mouse IL6 (22kDa).
Figure 2A:
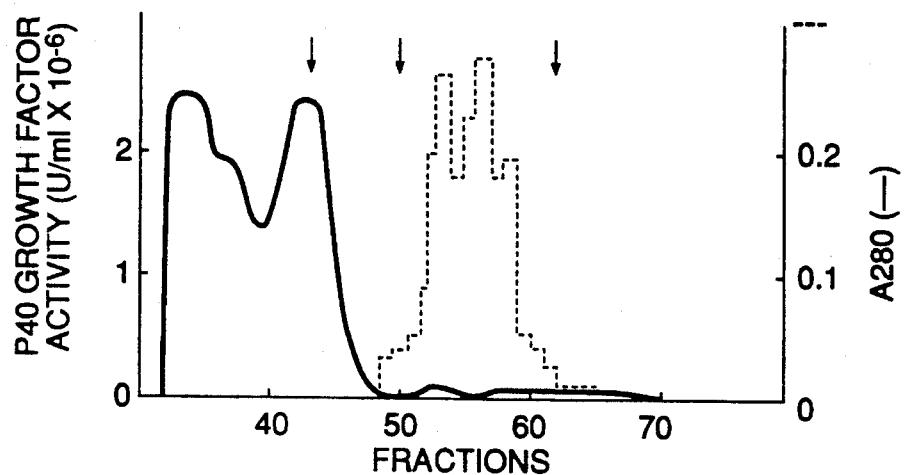

Large batches of T cell SN are produced by stimulating TUC2.15 and TUC7.51 cells with ConA as described in Example 1. The active material is concentrated by adsorption to silicic acid and applied to an Ultrogel AcA54 gel filtration column. The major growth promoting activity, which is destroyed by trypsin, elutes as a symmetrical peak in the 30–40 kDa region (FIG. 2A), and is therefore designated P40. Subsequent experiments are carried out with TUC7.51 SN because the concentrations of P40 are higher in this material.

Figure 3:
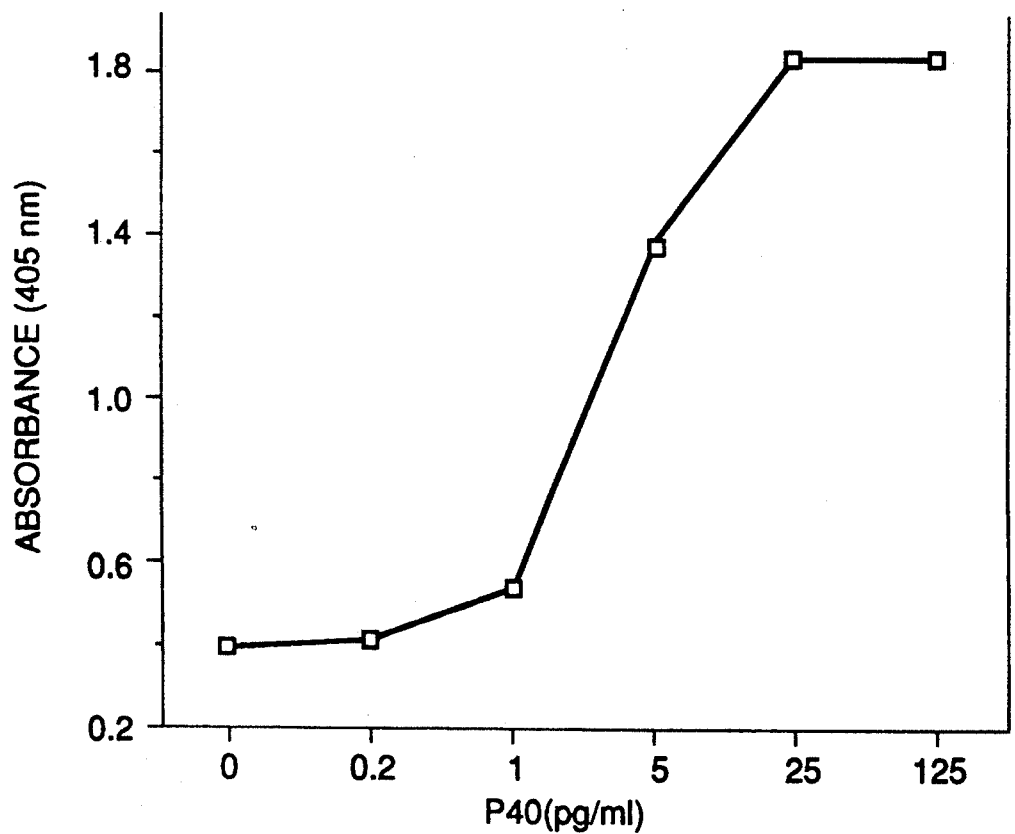
FIG. 3 is a graphical representation depicting growth factor activity of purified P40. TS1 cells ($3 \times 10^3$ cells/well) are cultivated in the presence of increasing doses of purified P40. After 3 days, cells numbers are evaluated by measuring hexosaminidase levels.
Figure 2B:
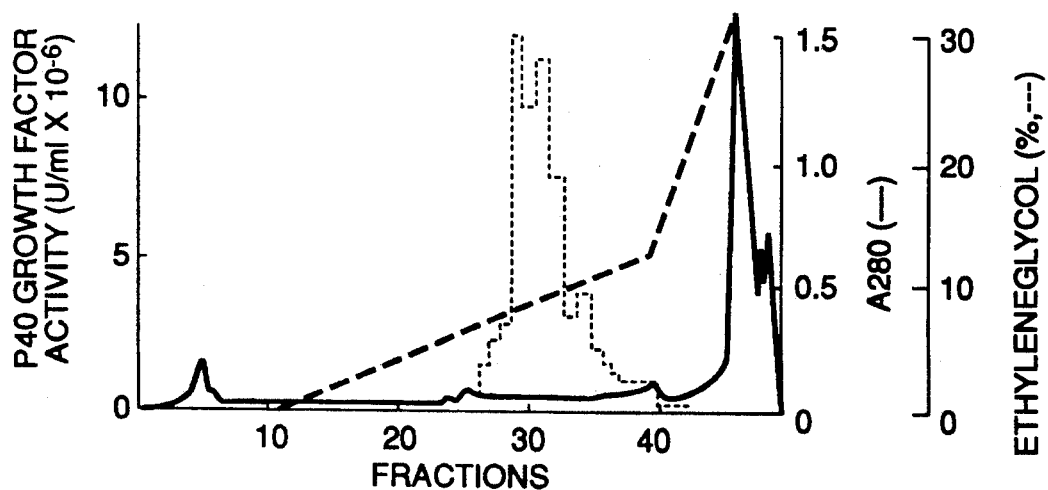
Figure 2C:
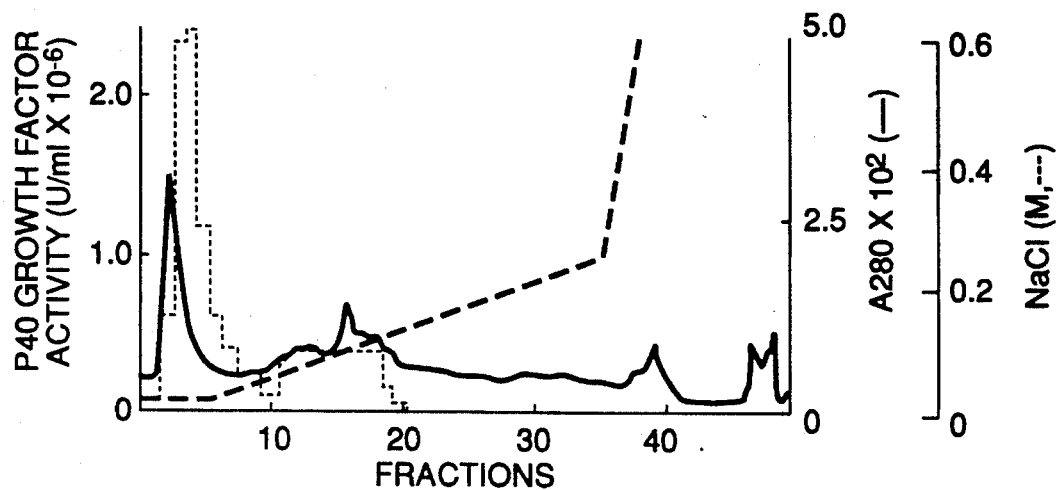
Figure 2D:
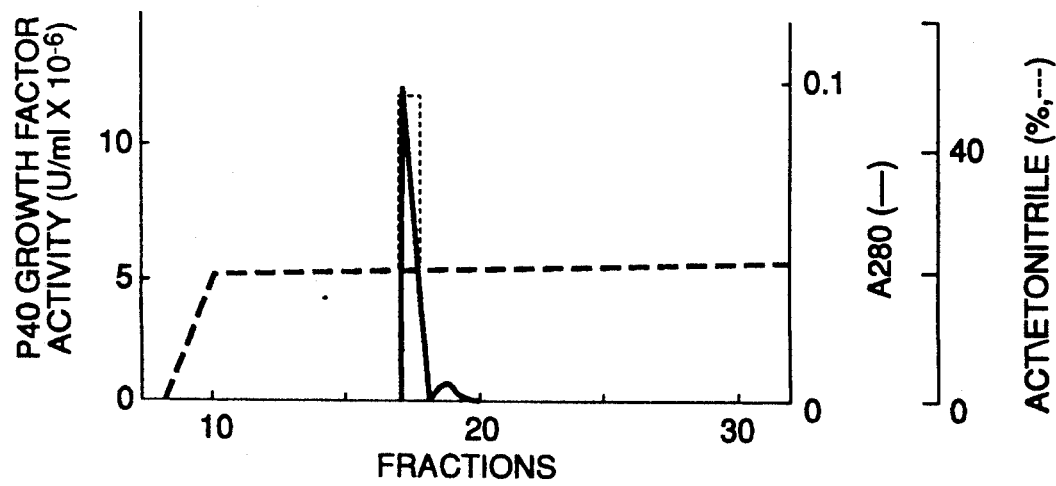

Preliminary characterization of the growth factor indicates that it has a pI of ~10 and is glycosylated, 60% of the activity being retained on a lentil lectin column. Based in part on this information, the following purification protocol is adopted. Active fractions from the gel filtration step are further separated by hydrophobic interaction chromatography on a TSK-phenyl column (FIG. 2B) followed by passage through a MonoQ anion exchange column equilibrated at pH 9.5. At this elevated pH, most contaminants are retained on the column, whereas P40 elutes mainly in the flow-through fractions, as expected from its high pI (FIG. 2C). Final purification is achieved by reversed phase chromatogrpahy on a C1-column equilibrated with 0.05% (w/v) TFA. P40 is recovered in a single peak eluting at an acetonitrile concentration of 35% (v/v) (FIG. 2D). At the end of this purification, P40 stimulates half-maximal growth of TS1 at a concentration of ~5 pg/ml (FIG. 3), which corresponds to a 2000- fold purification. On average, the overall yield ranges from about 5 to about 10%.

The purified protein is very heterogeneous with a Mr of about 32 to about 39 kDa in NaDodSO4/PAGE both under reducing (FIG. 4) and non-reducing conditions. Biological activity is recovered from the corresponding fractions of a non-reduced gel, but exposure to NaDodSO4 and 2-mercaptoethanol destroys most of the activity.

EXAMPLE 4

Amino Acid Sequence Analysis of Murine P40

Edman degradation of P40 ($\approx$250 pmol) did not yield N-terminal sequence. For sequence analysis, P40 (immobilized on the polybrene-treated sample disk of the sequencer) is acylated (Tarr, *Methods of Protein Microcharacterization* [ed. J. E. Shively] Human Press, pp. 155-194, 1986) and then subjected to in situ cyanogen bromide treatment as described by Simpson I. Sequence analysis is then continued and yields the following major amino acid sequence (110 pmol): NH2-Ala Gly Asn Thr Leu Ser Phe Leu Lys Ser Leu Leu Gly Thr Phe Gln Lys Thr Glu.

This internal sequence shows no significant similarity with that of other proteins stored in the data bases listed in Example 1.

The determination of the complete amino acid sequence was achieved by chemical methods.

Briefly, before proteolytic digestion native P40 was reduced with dithiothreitol and carboxymethylated with iodoacetic acid to yield Cm-P40. Peptides (indicated in FIG. 7) were prepared for sequence analysis by cleavage of Cm-P40 with endoproteinase Asp-N, trypsin, chymotrypsin, and cyanogen bromide (denoted by D, T, C, and N, respectively in FIG. 7). Subpeptides of the endoproteinase Asp-N were derived by cleavage with *Staphylococcus aureus* V8 protease (denoted with hyphenated S suffixes). In FIG. 7, amino acid residues not identified are indicated by X.

The exact methodology of amino acid sequence determination is described below:

A. Materials: Tween 20, guanadine hydrochloride (Sequenal grade) and trifluoroacetic acid (F3AcOH; 99+% pure grade) were purchased from Pierce Chemical Co. (Rockford, Ill., USA). Iodoacetic acid (puriss grade) was obtained from Fluka (Buchs, Switzerland) and was recyrstallized prior to use. Dithiothreitol was from Calbiochem (La Jolla, Calif., U.S.A.). Sodium chloride (Aristar grade) and acetic anhydride were purchased from BDH (Poole, UK). Cyanogen bromide (Univar grade) was from Ajax Chemical Co. (Sydney, Australia). All other chemicals were of the highest grade commercially available.

Trypsin (treated with tosylphenylethylchloromethane) and chymotrypsin were purchased from Worthington Biochemical Co. (New Jersey, USA). *Staphylococcus aureus* strain V8 protease was obtained from Miles Co. (Napperville, Ill., USA). Endoproteinase AspN from a *Pseudomonas fragi* mutant and N-glycanase F were obtained from Boehringer Mannheim GmbH (West Germany). All organic solvents were HPLC grade (Chromar grade, Mallinckrodt, Kentucky, USA). Deionized water, obtained from a tandem Milli-RO and Milli-Q system (Millipore, Inc., Mass., USA) was used for all buffers.

B. Preparation of murine S-carboxymethyl-P40 (Cm-P40): P40 (15 µg in 120 µl 35% aqueous acetonitrile containing 0.1% (v/v) F3AcOH and 0.02% Tween 20 was concentrated to approximately 10 µl by centrifugal centrifugation (Savant Ind. Hicksville, N.Y.), diluted to 160 µl with 7.5M guanidine.HCL containing 0.2M Tris.HCl buffer, pH 8.5, 0.002M EDTA and 0.02% (v/v) Tween 20 and then reduced with dithiothreitol (0.015M) at 40° C. for 4.5 h. Alkylation was achieved by the addition of iodoacetic acid (final concentration, 0.5M) to the mixture and incubation continued for 30 min at 25° C. in the dark. The reaction was halted by addition of 25 µl of 2-mercaptoethanol. Cm-P40 was recovered from the mixture using a reversed-phase high-performance liquid chromatography (RP-HPLC) procedure previously described (Simpson et al., *Eur. J. Biochem.* 1176:187-197, 1988 hereinafter Simpson II). The Cm-P40-containing fraction (60 µl) was adjusted to 0.02% (v/v) with respect to Tween 20 and then diluted to 1 ml with an appropriate buffer (containing 0.02% (v/v) Tween 20) prior to enzymatic digestion.

C. Trypsin digestion: Cm-P40 (7 ug) in 1 ml of 1% (w/v) NH4HCO3, pH 7.8 containing 0.001M CaCl2 and 0.02% (v/v) Tween 20 was digested with 0.5 µg trypsin for 16 h at 37° C.

D. Chymotrypsin digestion: Cm-P40 (6 µg) in 1 ml of 1% (w/v) NH4HCO3, pH 7.8 and 0.02% (v/v) Tween 20 was digested with 0.6 µg chymotrypsin for 16 h at 37° C.

E. Endoproteinase Asp-N digestion: Cm-P40 (15 µg) in 1020 µl of 0.05M sodium phosphate buffer, pH 8.1, 0.02% (v/v) Tween 20 was digested with 0.7 µg of freshly prepared endoproteinase Asp-N for 16 h at 34° C.

F. *Staphylococcus aureus* strain V8 protease digestion: Endoproteinase Asp-N peptide D3 in 1 ml of 1% (w/v) NH4HCO3, 0.02% (v/v) Tween 20 was digested with 0.5 µg *S. aureus* V8 protease at an enzyme/substrate ratio of 1:10 for 16 h at 30° C.

G. Purification of polypeptides by high-performance liquid chromatography instrumentation: Peptide mixtures resulting from enzymatic cleaves were fractionated by reversed-phase HPLC on a Hewlett-Packard liquid chromatograph (model 1090A) fitted with a diode-array detector (model 1040A) as described (Simpson II).

H. Column Supports: The following columns were used for the purification of Cm-P40 an derived peptides: (a) Brownlee RP-300 (300 nm pore size, 7-µm particle diameter, octylsilica packed into a stainless steel column 30×2.1 mm i.d. or 50×1 mm i.d., Brownlee Laboratories, Santa Clara, Calif., USA). (b) Dimethylaminoazobenzene sulfonyl chloride (DABS-Cl) amino acids were separated and quantitated on a Brownlee PTC amino acid analysis column (220×2.0 mm i.d.) (Applied Biosystems, Foster City, Calif., USA).

I. Peptide nomenclature: The following prefixes are used to denote the origin of various peptides: T, Trypsin; CN, cyanogen bromide; C, chymotrypsin; D, endoproteinase Asp-N. Peptides resulting from sub-digestion of endoproteinase Asp-N peptides with *S. aureus* V8 protease are denoted by hyphenated S suffixes. Peptides are numbered in the order of their positions in the final sequence.

J. Cyanogen bromide cleavage: After P40 (10 μg) was subjected to several cycles of Edman degradation in the protein sequencer without any detectable PTH-amino acids, the sequence analysis was stopped. In situ cyanogen bromide cleavage of native P40 was performed on the glass fiber sample disk of the protein sequencer according to a procedure previously described (Simpson, I). Sequencer background levels which had arisen during the sequence analysis were reduced by treating the sample disk with 30 μl aqueous 50% (v/v) N-ethylmorpholine followed by 10 μl acetic anhydride (60 min at 25° C.). The filter was vacuum dried and then treated with a 20-fold excess of cyanogen bromide in 70% (v/v) formic acid for 15 h at 25° C. At the end of this time the sample filter was vacuum dried for 30 min and the sequence analysis continued.

K. Amino acid sequence analysis: Automated Edman degradation of protein and peptide was performed using Applied Biosystems sequencers (models 470A and 477A) equipped with on-line phenylthiohydantoin (Pth) amino acid analyzers (model 120A). Total Pth-amino acid derivatives from the sequencer were injected onto the liquid chromatograph using a modified sample transfer device as described [Begg et al., in "Techniques in Protein Chemistry", (Hugli, T. E., Ed.) Academic Press, Orlando Fla., USA, in press]. Polybrene was used as a carrier.

EXAMPLE 5

Peptide purification by microbore RP-HPLC

Figure 8:
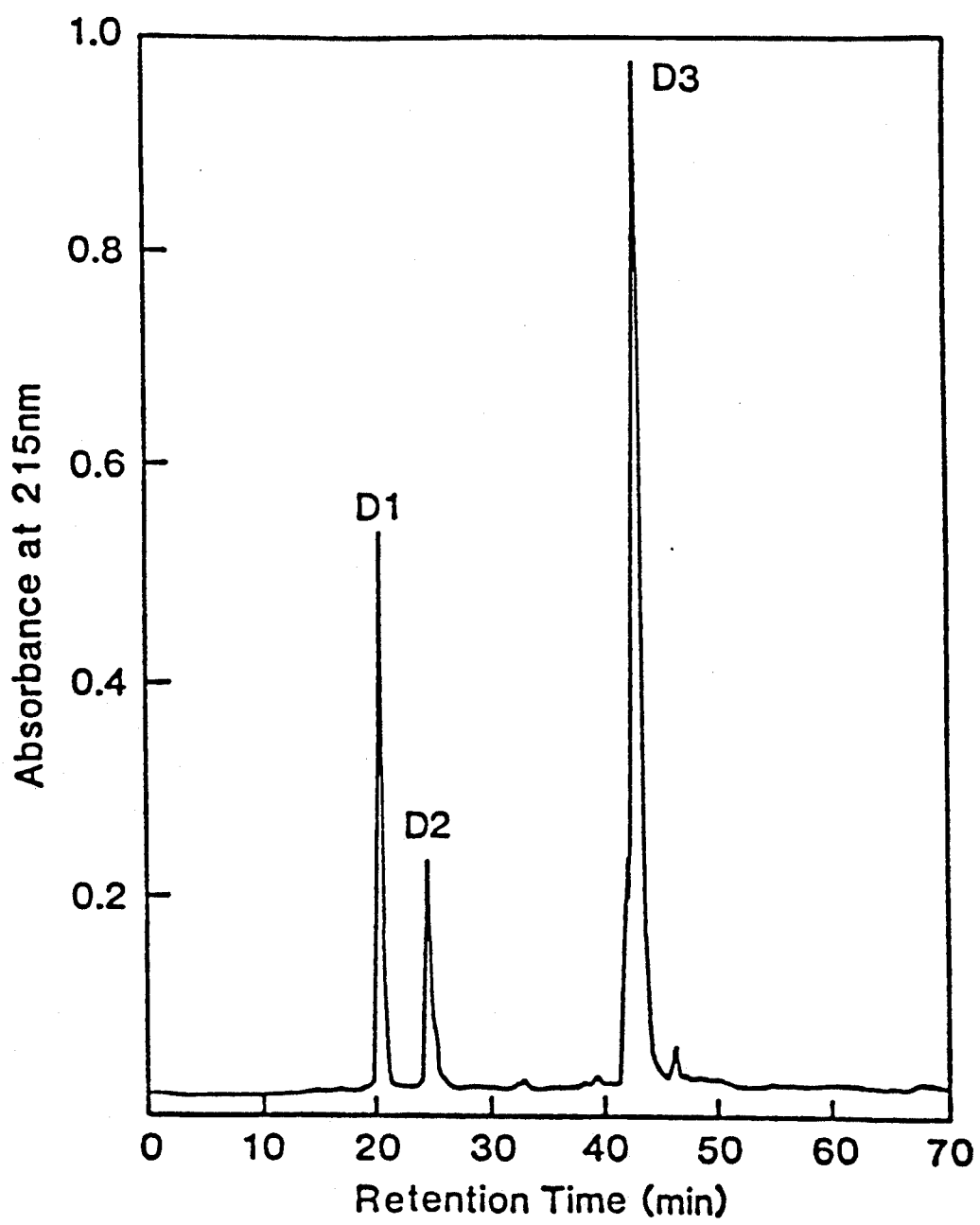
FIG. 8 is a graphic illustration of the separation of endoproteinase Asp-N peptides of Cm-P40 by RP-HPLC.
Figure 9:
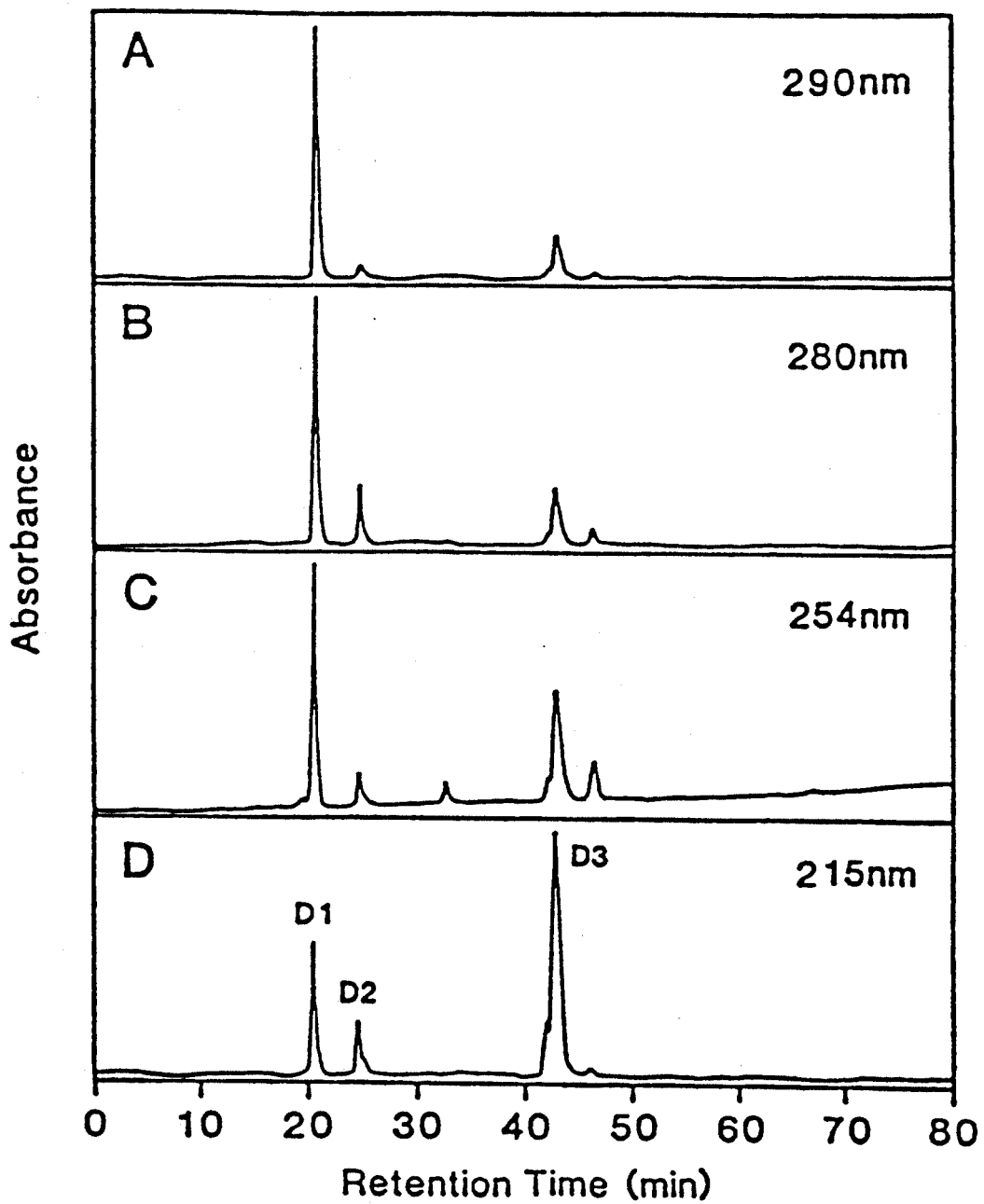
FIGS. 9A-9D is a graphic illustration of a multiwavelength plot of the HPLC profile of FIG. 8 using a hotodiode array detector at wavelengths of (A) 290 nm, (B) 280 nm, (C) 254 nm and (D) 215 nm.
Figure 10:
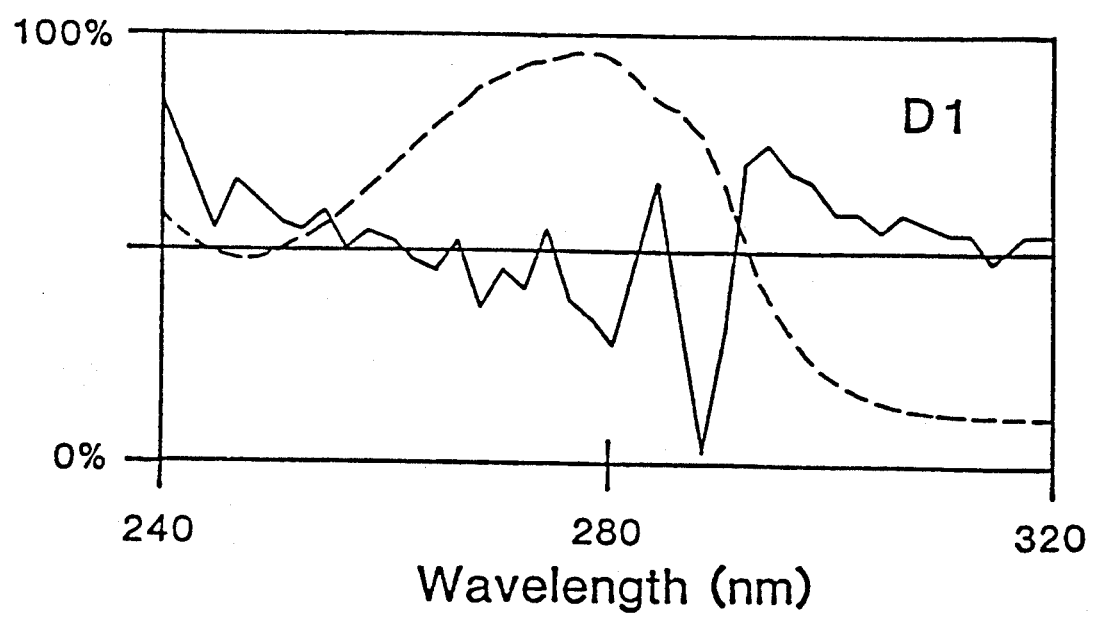
FIG. 10 is a graphic illustration of a derivative spectral analysis of endoproteinase Asp-N peptide D1 with the zero order spectrum indicated by (--) and the second order spectrum indicated by (—).
Figure 11A:
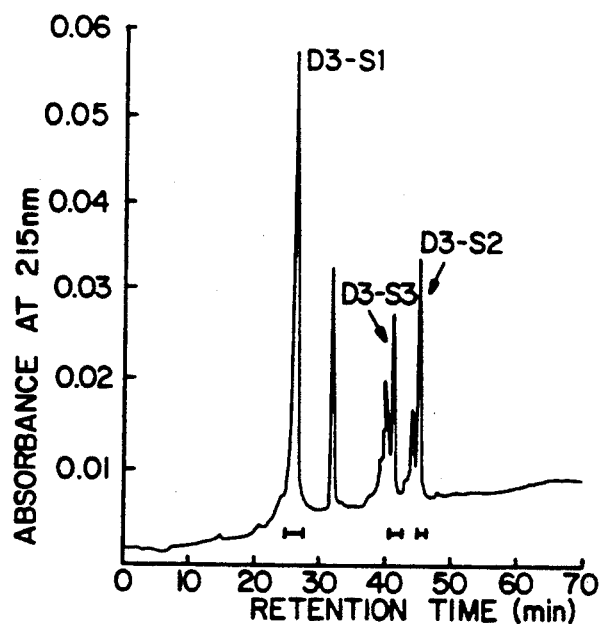
FIGS. 11A-11C is a graphic illustration of the microbore RP-HPLC separation of peptides of Cm-P40 derived from digestion with various proteases. Panel A shows the peptides from S. aureus V8 protease digestion of Cm-P40 endoproteinase Asp-N peptide D3. Panel B shows the peptides from a chymotrypsin digestion of Cm-P40. Panel C shows the peptides from a trypsin digestion of Cm-P40.

Cm-P40 (15 μg) was digested with endoproteinase Asp-N and the digest fractionated by RP-HPLC on a short microbore column (30×2.1 mm i.d.), employing a low-pH ($F_3$AcOH, pH 2.1) mobile phase and a gradient of acetonitrile. Three major peptide-containing peaks were detected: D1, D2 and D3 (FIG. 8). Spectral analyses of these peptides were performed using real-time photodiode-array spectroscopy and the absorption spectra of peptides D1, D2 and D3 are shown in FIG. 9. The high absorbance at 290 nm of peptide D1 is indicative of the presence of a tryptophan residue. The D2 and D3 peptides have high absorbance at 280 nm and low absorbance at 290 nm which is characteristic of tyrosine-containing peptides. The presence of tryptophan residue in peptide D1 is supported by the derivative absorbance spectrum shown in FIG. 10. Enhancement of resolution by second-order-derivative spectroscopy reveals extrema at 290; 2 nm and 280±2 nm which are characteristic of tryptophan residues. Peptide D3 was subdigested with *S. aureus* V8 protease and the resultant digest fractionated by RP-HPLC at low pH ($F_3$AcOH) (FIG. 11A).

Figure 11B:
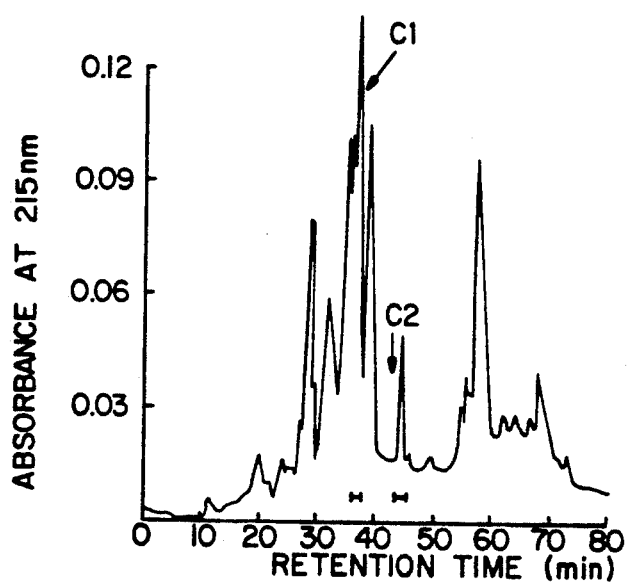
Figure 11C:
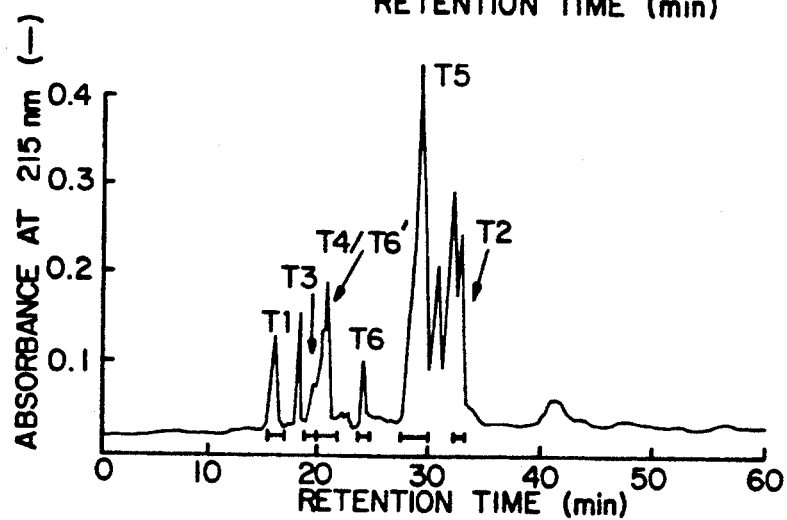

Reversed-phase HPLC purification of peptides resulting from treatment of Cm-P40 with chymotrypsin and trypsin were performed and analyzed in a similar manner. Reversed-phase fractionation of these digests, however, resulted in a complex pattern of peptide-containing peaks (FIGS. 11B and 11C). All of the peptide fractions from the first dimension RP-HPLC were subjected to a second chromatographic step using the same chromatographic support and acetonitrile gradient but a different mobile phase (e.g., unbuffered sodium chloride or 20 mM sodium phosphate, pH 7.0). For some peptides a third chromatographic step was necessary before a homogeneous peptide could be isolated. In the latter situation, an ODS-hypersil column and a different organic solvent (methanol) were used for the chromatography (Simpson II).

EXAMPLE 6

Characterization of glycosylation state of P40

Cm-P40 (0.5 μg) was iodinated using the iodine monochloride procedure. $^{125}$I-Cm-P40 was separated from free $^{125}$I by sequential gel filtration and cation-exchange chromatography. $^{125}$I-Cm-P40, untreated, reduced with 2-mercaptoethanol for 5 min at 95° C., or digested with N-glycanase F (Genzyme, Boston, Mass. USA) or endo-α-N-acetylgalactosaminidase (O-glycan-peptide hydrolase, Boehringer Mannheim) for 16 h at 37° C. according to the manufacturers' instructions was electrophoresed on a 10–15% gradient polyacrylamide gel in the presence of SDS. The gel was stained with Coomassie Blue R250 using the Phast electrophoresis sytem (Pharmacia, Uppsala, Sweden) according to the manufacturer's instructions. $^{125}$I-Cm-P40 was detected by autoradiography using Hyperfilm, MP (Amersham, Buckinghamshire, UK).

Figure 4A:
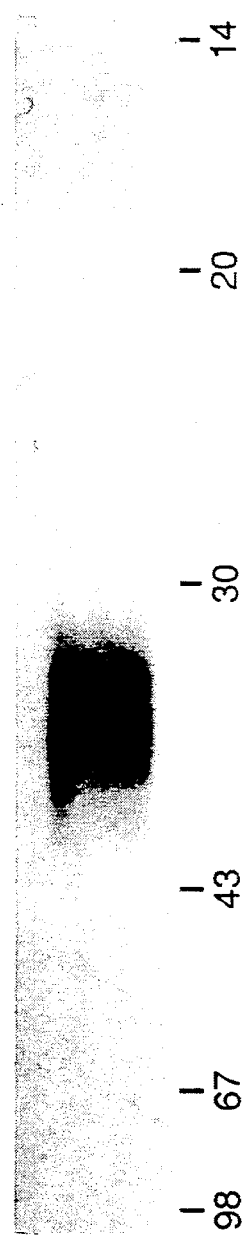
Figure 4B:
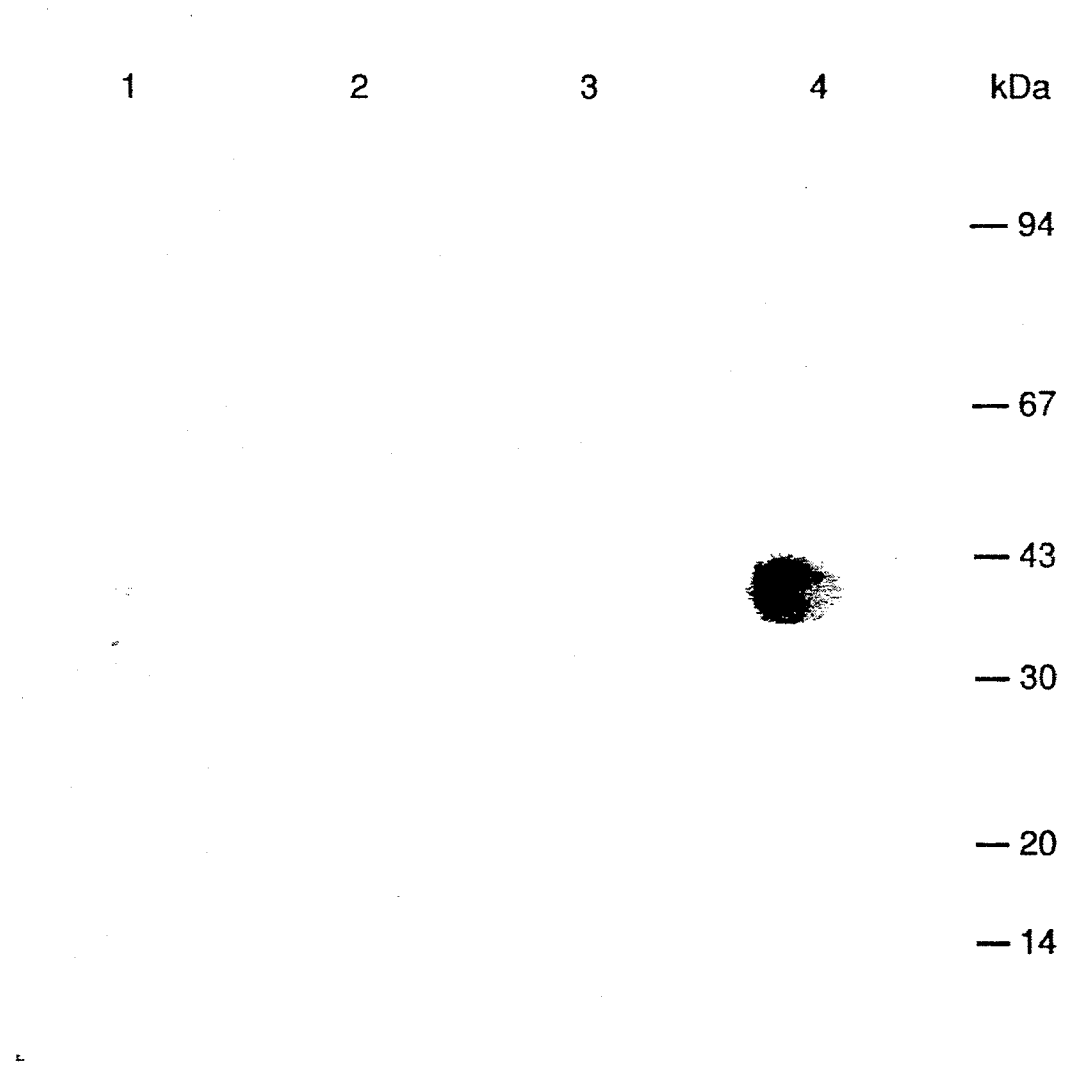

Purified iodinated P40 electrophoresed as a single broad band of apparent $M_r$ 32,000–39,000 daltons on 12% SDS-PAGE in both the unreduced and reduced (2-mercaptoethanol) state (see FIG. 4, Lane 1 and 4) indicating that it is a monomeric protein. Endo-α-N-acetylgalactosaminidase (O-glycanase) treatment of P40 had no apparent effect on the molecular mass (FIG. 4, Lane 3) but treatment with N-glycanase F caused a reduction in apparent $M_r$ to 15,000–16,000 Da (FIG. 4, Lane 2). The lack of effect of O-glycanase indicates that P40 does not contain O-linked carbohydrate chains or that these sites are not accessible in the intact molecule. Since N-glycanase F releases carbohydrate moieties attached to asparagine residues (N-linked) this indicates that P40 consists of a protein core ($M_r$ 15,000–16,000) with considerable amounts of N-linked sugars.

Murine P40 has 126 amino acids. The calculated $M_r$ from the sequence analysis is 14,150. The difference in the calculated $M_r$ and the measured $M_r$ for native P40 (32–39 kDa) can be attributed to N-glycosylation since upon treatment with N-glycanase F the $M_r$ is reduced to 15,000–16,000 (FIG. 4). The protein sequence data provides information on the post-translational processing of mature P40. For instance, since no amino acid was identified at positions 32, 60, 83 and 96 (FIG. 10) and since these positions meet the criteria for N-linked glycosylation sites (i.e. Asn-Xaa-Thr/Ser), these data are consistent with asparagines being glycosylated at these four positions. Confirmation of asparagine residues at positions 32, 60, 83 and 96 and the COOH - terminal residue (Pro-126) was provided by sequence analysis of a P40 cDNA clone.

EXAMPLE 7

Analysis of N-terminal block in murine P40

The exact nature of the blocked N-terminus was determined by a combination of amino acid analysis, fast-atom-bombardment mass spectrometry, and peptide synthesis. These analyses indicated the N-terminus of murine P40 is likely to be pyroglutamic acid.

The methods involved in determining the amino terminal residue of P40 and a discussion thereof follow:

Method

A. Amino acid analysis: Amino acid analysis was performed on a Beckman amino acid analyzer (model 6300) equipped with a model 7000 data system or by using the dimethylaminoazobenzene sulfonyl chloride (DABS-Cl) precolumn derivatization procedure using microbore column RP-HPLC (Simpson, et al., *Euro. J. Biochem.* 153: 629-637, 1985). Samples were hydrolyzed in vacuo at 110° C. for 24 h with gaseous HCl generated from 6M HCl containing 0.1% (w/v) phenol.

B. Fast-atom-bombardment mass spectrometry: Fast-atom-bombardment mass spectrometry (Barber et al., *Anal. Chem.*, 54: 645A-657A, 1982) was performed using a VG 70/70E-HF forward-geometry double-focussing means spectrometer (VG Analytical, Manchester, UK) equipped with an Ion Tech saddle-field fast-atom gun. Sample was applied in 2 μl of 0.1% (v/v) aqueous $F_3AcOH$ to the sample stage containing 1 μl of pre-applied mixture of dithiothreitol/dithioerythritol (5:1). Xenon atoms at a potential of 8 keV and a discharge potential of 1 mA were used for sample bombardment. Scans were performed at 40 s/decade at a resolution of 1500. Positive-ion spectra were acquired by multi-channel analysis mode using a VG 11/250J data system.

C. Peptide synthesis: Fluorenylmethoxycarbonyl (Fmoc)-polyamide solid phase peptide chemistry was employed to synthesize two peptides corresponding to the N-terminal decapeptide of P40 (endoproteinase Asp-N peptide D1) with either glutamic acid or glutamine as the amino terminal residue. The conventional Fmoc polyamide side chain protecting groups were employed: Trp (CHO); Arg (Mtr), Mtr=4-methoxy-2,3,6,-trimethylbenzenesulfonyl); Glu (OtBu); Cys (tBu). Pentafluorophenyl (OPfp) esters of all Fmoc-amino acids in dimethylformamide with the exception of Fmoc-Arg (MtC) which was activated as an 1-hydroxybenzotriazole (HOBt) ester, were employed for sequential coupling of activated amino acids on RaMPS (DuPont, N.J.) Wang resin. Peptide bond formation was generally complete within 120 min provided that the concentration of the OPfp ester was 2.5× times greater than the concentration of derivatized resin and provided that one equivalent of 1-hydroxybenzotriazole was added to the coupling mixture in order to catalyze the reaction. Upon completion of the synthesis, the peptide was deprotected and cleaved from the resin by extended treatment with $F_3AcOH$ (containing 5.4% thioanisol, 0.6% 1,2-ethanedithiol). Crude synthetic peptides and their derivatives (e.g. S-carboxymethyl-peptides) were purified by reversed-phase HPLC. The pure synthetic peptides chromatographed as single peaks on reversed-phase HPLC (Brownlee RP-300 column 30×2.1 mm, i.d.) and gave the expected amino acid ratios.

Peptides (30 μg in 100 μl 0.1% $F_3AcOH$) were acetylated with acetic anhydride by treatment with 6 μl N-ethylmorpholine (Pierce, sequenal grade) followed by 2 μl acetic anhydride (Fluka, puriss grade) for 10 min at 25° C. Formation of pyroglutamyl peptides was accomplished by treating the glutamine peptide at 110° C. for 16 h at pH 7.8 under nitrogen.

Discussion

Analysis of three major Asp-N peptides (D1-D3) and the *S. aureus* V8protease subpeptides of D3 provided 65% of the P40 amino acid sequence. Of the three peptides, D1, the single tryptophan-containing peptide was $N^\alpha$ blocked, indicating that this peptide was derived from the N-terminal portion of the polypeptide chain. The amino acid composition of the N-blocked Asp-N peptide D1 was consistent with the trytophan-containing tryptic peptide T1 with the N-terminal addition of two extra residues (Glx and Arg).

Figure 12:
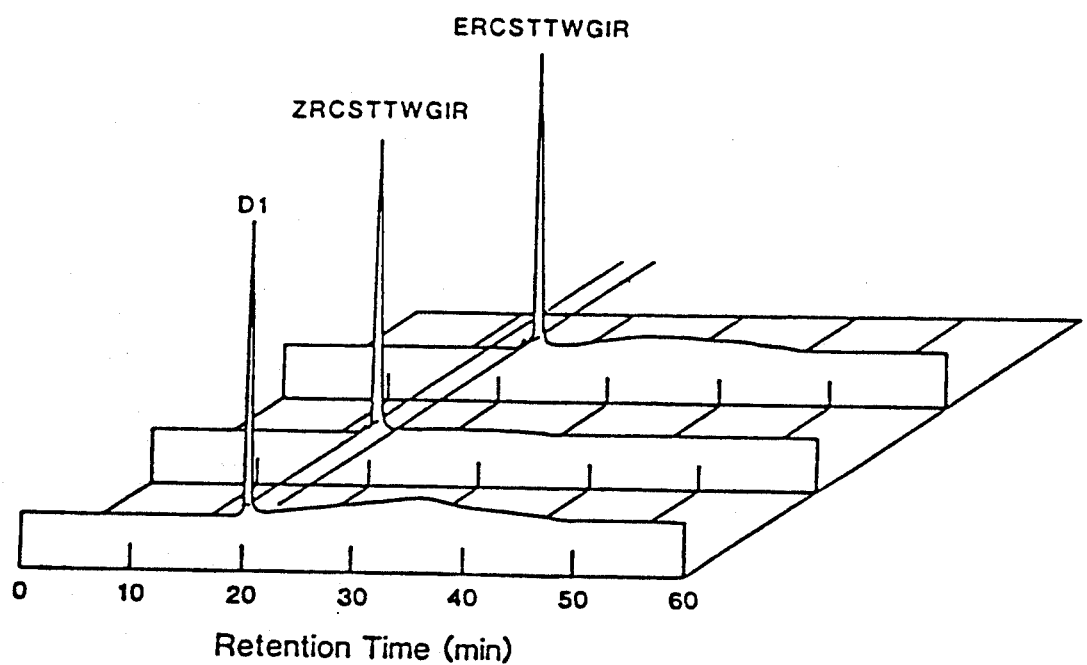
FIG. 12 is a graphic illustration of the elution profile of the blocked amino terminal peptide D1 and related synthetic peptides on RP-HPLC. Z indicates pyroglutamic acid.

Fast-atom-bombardment mass spectrometry (FAB-MS) of Asp-N peptide D1 revealed a protonated molecular ion (MH+) of mass 1248 which only corresponds to the amino acid composition of this peptide if the blocking group was assumed to be pyroglutamic acid. The nature of the N-blocking group was examined using two synthetic decapeptides D1 with either glutamic acid or glutamine at the amino terminus (see FIGS. 7 and 12). As shown in FIG. 12, the endoproteinase Asp-N peptide D1 and the pyroglutamyl synthetic peptide co-chromatographed on reversed-phase HPLC (retention time, 20.50±−0.2 min) and were well resolved from the glutamyl synthetic peptide (retention time, 22.70±0.2 min). after acetylation, the chromatographic behavior of D1 and the pyroglutamyl synthetic peptide was identical (no increase in retention time) while the acetylated glutamyl synthetic peptide exhibited a marked increase in retention behavior (retention time was 28.97±0.2 min compared to the non-acetylated form, 22.70±0.2 min). The amino terminus of P40 is likely to be pyroglutamic acid since the amino-terminal endoproteinase Asp-N peptide D1 behaves in exactly the same manner as the synthetic pyroglutamyl peptide before and after acetylation on reversed-phase HPLC. FAB-MS of the glutamyl synthetic peptide yielded a molecular mass of 1248 which was in perfect agreement with that obtained for Asp-N peptide D1.

EXAMPLE 8

Biological Activity of Purified P40

Purified P40, at concentrations up to 20 ng/ml, did not support the proliferation of either IL3-dependent myeloid cell lines (FDCP-1, Ea3.15 and DA-1), IL5-dependent B cell lymphoma BCL1, or IL6-dependent B cell hybridoma 7TD1. Unlike IL2, and to some extent IL4, it also fails to stimulate any of six cytolytic T cell clones tested (Table 3). By contrast, strong proliferations are observed with some but not all helper T cell lines. Both IL2-producing ($TH_1$ type, TUC7.33) and IL4-producing ($TH_2$ type, e.g., TUC2.15) clones are found among the responders. A significant correlation, illustrated in Table 3 for clone TUC7.51, is observed between the time spent in culture and the responses to P40 and IL4.

TABLE 3

Comparison of the T Cell Growth Factor Activities of IL2, IL4, and Purified P40

| T Cell Lines and Clones | Proliferation in response to[a] | | |
|---|---|---|---|
| | IL2 | IL4 | P40 |
| Cytolytic T Cells | | | |
| CTLL-2 | 445 | 0.6 | 0.8 |
| P35:10 | 683 | 24 | 1.2 |
| P35:48 | 303 | 4 | 1.8 |
| P91:6 | 195 | 2 | 1.6 |
| P1:5 | 993 | 12 | 1.2 |
| P1:204-8 | 630 | 9 | 1.2 |
| Helper T Cells | | | |
| TUC2 | 311 | 2 | 14 |
| TUC2.15 | 1,806 | 813 | 240 |
| TUC5 | 263 | 20 | 13 |
| TUC5.37 | 253 | 4 | 0.8 |

TABLE 3-continued

Comparison of the T Cell Growth Factor
Activities of IL2, IL4, and Purified P40

| T Cell Lines and Clones | Proliferation in response to[a] | | |
|---|---|---|---|
| | IL2 | IL4 | P40 |
| TUC7.33 | 115 | 276 | 235 |
| TUC7.51[b] | 1,179 | 27 | 17 |
| TUC7.51[c] | 1,345 | 634 | 199 |
| TUC13.1 | 116 | 51 | 1.7 |

A) Cells are incubated with or without the indicated growth factors and thymidien incorporation is measured on day 3. Factor dosage is as follows: 100 U/ml for IL2 and IL4, and $10^3$–$10^4$ U/ml for P40. The results are shown as ratios of radioactivity incorporated with and without factors.
B) 1 month-old culture
C) 1 year-old culture

EXAMPLE 9

Cloning and Characterization of the Murine P40 Gene

Screening of cDNA library. Double-stranded cDNA was prepared according to Gubler, et al., *Gene* 25: 263, 1983, using polyadenylated RNA isolated from P40-producing helper T cells TUC7.51 after a 24 h stimulation with ConA (2.5 μg/ml). The cDNA was cloned into the BamHI site of a pUC8 vector and transformed into *E. coli* strain DH5. Transformants were screened by in situ hybridization with two end-labeled 20-mer oligonucleotide probes. For the initial screening, a 64-fold degenerate probe [5'-TGCAT(C+T)TC(X)GT(C+T)TT(C+T)TG(-G+A)AA−3'] corresponding to amino acid sequence FQKTEMQ (positions 114–120, see text) was used. Positive clones were subsequently tested with a 129-fold degenerate probe [5'-GG(A+G)T-C(A+G)TC(T+C)TT(X)AG-(A+G)TT(C+T)TC−3'] corresponding to sequence ENLKDDP (positions 17–23, see text).

Figure 5:
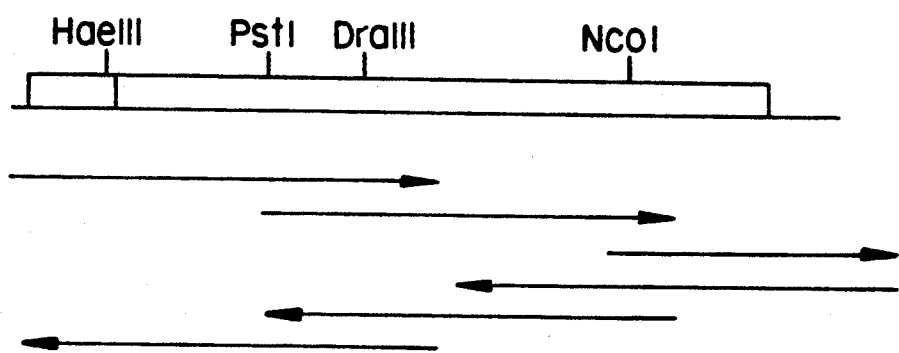
FIG. 5 is a graphic illustration of the sequencing strategy of the murine P40 gene.

DNA sequencing. DNA was sequenced by the dideoxynucleotide procedure after subcloning into a M13 vector. Appropriate fragments were generated by digestion with PstI and NcoI restriction endonucleases using the sequencing strategy shown in FIG. 5.

Characterization of cDNA and Construction of Expression Vectors. A cDNA library was prepared, in a pUC8 vector, from a helper T cell clone that produces large amounts of P40 after stimulation with ConA. This library was screened with two oligonucleotide probes synthesized on the basis of selected amino acid sequence data obtained by analysis of P40 peptides. Of 20,000 independent tranformants, 112 hybridized with the two probes. Most of these clones contained cDNa inserts of about 500 bp. Using one of these cDNA's as a probe, a strong signal was obtained with a transcript of about 700 nucleotides in Northern blots of poly(A)+RNA isolated from P40-producing helper T cell clone TUC7.51. Poly (A)+RNA from P815 mastocytoma, which does not produce detectable P40 activity, gave no signal at all.

Figure 6:
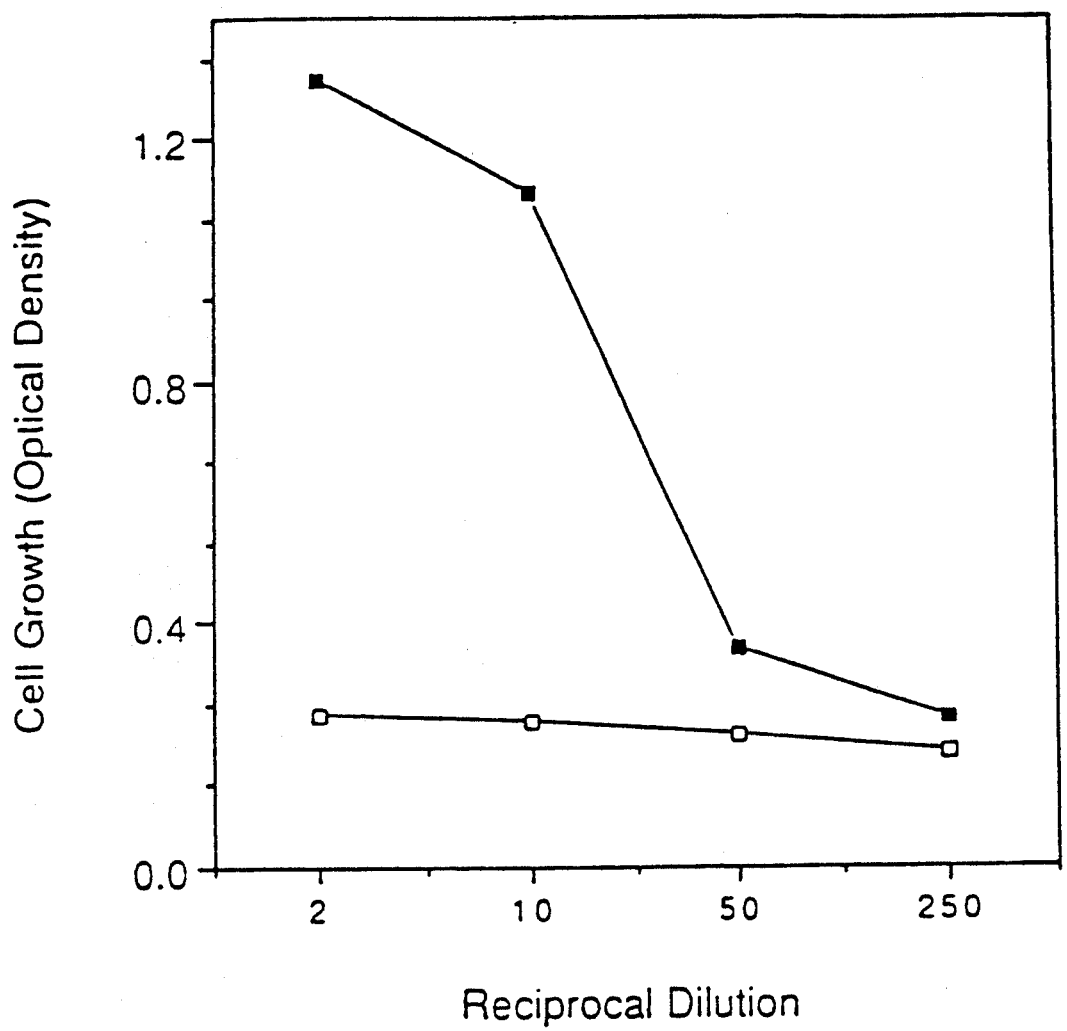
FIG. 6 is a graphic illustration of the expression of recombinant P40 in fibroblasts.

To establish that the selected cloned contained authentic P40 cDNA, an expression vector was constructed. Insert P40.2B4 was cloned into BamHI site of plasmid pZIPneoSV(X)1 (Cepko, et al., *Cell* 37: 1053, 1984) and transfected into Clone-1d fibroblasts (Kit, et al., *Exp. Cell. Res.* 31: 297, 1963). Cell supernatants collected 48 h after transfection were tested for their growth factor activity on P40-dependent TS1 cells. as shown in FIG. 6, supernatants form cells transfected with P40.2B4 cDNA (closed symbols), but not from mock-tranfected cells (open symbols), supported the growth of TS1. This result indicates that P40.2B4 cDNa presumably contains the entire coding region of P40.

The complete nucleotide sequence of the cDNA insert of clone P40.2B4 was determined, and is shown under "Detailed Description of the Invention". It consists of 554 nucleotides with a 5' untranslated sequence of 15 nucleotides, an open reading frame of 432 nucleotides and a 3' untranslated region of 107 nucleotides. The 3'-end terminates with a string of 18 adenine residues located 12 nucleotides downstream from an AA-TAAA polyadenylation signal consensus sequence. The 3'untranslated region contains 3 copies of the sequence ATTTA which is characteristic of transiently expressed genes such as GM-CSF, G-CSF, interferons, several interleukins, tumor necrosis factor, and oncogenes c-fos and c-myc (Shaw et al., *Cell* 46: 659, 1986); two of these repeats at nucleotide positions 461–468 and 470–477 are part of an 8 nucleotide motif TATTTATT, which is also present in many of these molecules (Caput et al., *Proc. Natl. Acad. Sci. USA* 83: 1670, 1986).

The predicted polypeptide encoded by the cDNA insert of clone P40.2B4 consists of 144 residues. This size estimation is based on the presumption that the first ATG in the sequence (nucleotide position 16–18) is the initiator codon, a view supported by the efficient expression of the cDNA in fibroblasts and by the presence of an adenine at nucleotide position 13, in concordance with the consensus sequence for an initiator ATG codon; an in-frame TGA translation termination codon occurs as nucleotides 448–450. The deducted P40 sequence is characterized by a hydrophobic N-terminal sequence typical of a signal peptide. Because of the presence of a blocked N-terminus in the native protein, there is some uncertainty concerning the N-terminal residue. Based on the probability weight-matrix described, (Von Heijne, *Nucleic Acid Res.* 14: 4683, 1986), the most likely N-terminal sequence of the mature protein would be Gln-Arg-Cys . . . This is consistent with evidence obtained by biochemical analysis of P40 peptides. Mature P40 would then consist of 126 amino acids with a predicted relative molecular mass of 14,150. The difference with the Mr measured for native P40 appears to be due to glycosylation as suggested by the presence of 4 potential N-linked glycosylation sites and confirmed by the about 15kDa Mr of the native protein after N-glycanase-treatment. The sequence of P40 is further characterized by the presence of 40 cysteines and a strong predominance by cationic residues, which explains the elevated pI(10) of the native protein.

EXAMPLE 10

Isolation of the Human Genomic P40 Gene

The human genomic P40 gene was cloned using the murine a P40 cDNA clone as a probe. Briefly, a human genomic library was constructed in phage λGEMII with Sau3A-cut DNA isolated from an EBV-immortalized lymphoblastoid cell line (CESS). A resulting clone (λH403A1) was isolated by cross-hybridization with the murine P40 cDNA.

EXAMPLE 11

Isolation of the Human cDNA for P40

A cDNA library was constructed with poly-A+RNA prepared from peripheral blood mononuclear cells stimulated for 24 h with phytohemagglutinin and phorbol myristate acetate. The library was screened with a restriction fragment of the human genomic clone described in Example 10. One of the positive clones was sequenced by the methods described in Example 10, and the DNA sequence with its deduced amino acid sequence is shown under the "Detailed Description of the Invention". Sequence analysis indicated that the murine and human P40 amino acid sequences are 55% homologous.

EXAMPLE 12

Synergistic Effect of P40 and IL4 or IL3

The proliferative effects of co-culturing helper T cells in the presence of P40 and IL4 or Il3 was investigated. TUC2.15N and TUC7.41 cells ($5 \times 10^4$/well) were cultured with suboptimal amounts of P40 in the presence or absence of a suboptimal dose of IL4 or close to optimal dose of IL3. After 3 days in culture, the cells were pulsed with tritiated thymidine. The results in Table 4 indicate that the helper T cells treated with P40 and IL4 or P40 and IL3 incorporated from about 4-40 times more thymidine that those cells treated with any one of these proteins. Thus, a strong synergy between P40 and IL4 or IL3 exists with respect to stimulating proliferation of helper T cell lines that respond to these proteins.

TABLE 4

Synergism between P40 and IL4 or IL3

| Cells | P40 (U/ml) | IL4 (U/ml) | IL3 (ng/ml) | Thymidine Incorporation (cpm) |
|---|---|---|---|---|
| TUC2.15N | 0 | 0 | 0 | 122 |
| | 80 | 0 | 0 | 1296 |
| | 0 | 20 | 0 | 4446 |
| | 80 | 20 | 0 | 19248 |
| | 0 | 0 | 3 | 4781 |
| | 80 | 0 | 3 | 54366 |
| TUC7.51N | 0 | 0 | 0 | 120 |
| | 80 | 0 | 0 | 4958 |
| | 0 | 20 | 0 | 4459 |
| | 80 | 20 | 0 | 31050 |
| | 0 | 0 | 3 | 4354 |
| | 80 | 0 | 3 | 72157 |

TUC2.15N and TUC7.51 helper T cells ($5 \times 10^4$/well) were cultured with suboptimal amounts of P40 in the presence or absence of a suboptimal dose of IL4 or of an optimal dose of IL3. The cultures were pulsed with tritiated thymidine after 3 days.

What is claimed is:

1. Antibody which specifically binds to mammalian T cell growth factor P40, wherein said mammalian T cell growth factor: (i) supports interleukin-2 and interleukin-4 independent growth of helper T cells, and (ii) has a molecular weight of from about 30 kDa to about 40 kDa.

2. Antibody of claim 1, wherein said antibody is a monoclonal antibody.

3. Antibody of claim 1, wherein said antibody specifically binds to murine T cell growth factor P40.

4. Antibody of claim 3, wherein said antibody is a monoclonal antibody.

5. Antibody of claim 1, wherein said antibody specifically binds to human T cell growth factor P40.

6. Antibody of claim 5, wherein said antibody is a monoclonal antibody.

* * * * *

UNITED STATES PATENT AND TRADEMARK OFFICE
CERTIFICATE OF CORRECTION

PATENT NO. : 5,157,112
DATED : October 20, 1992
INVENTOR(S) : Jacques Van Snick, et. al.

It is certified that error appears in the above-indentified patent and that said Letters Patent is hereby corrected as shown below:

Column 1, line 67, change "of $T_{H}2)$" to -- of $T_H(T_H2)$ --.
Column 5, line 55, change "Il3" to -- IL3 --.
Column 11, line 55, change "scan" to -- can --.
Column 14, line 58, change "helpter" to -- helper --.
Column 20, line 27, change "8" to -- 18 --.
Column 24, line 55 change "Cm-P40 an" to --Cm-P40 and--.
Column 28, line 21, change "after" to -- After --.
Column 29, line 66, change "form" to -- from --.

Signed and Sealed this

Fifteenth Day of March, 1994

Attest:

BRUCE LEHMAN

Attesting Officer     Commissioner of Patents and Trademarks